US008769002B2

(12) United States Patent
Katsuki et al.

(10) Patent No.: US 8,769,002 B2
(45) Date of Patent: Jul. 1, 2014

(54) INFORMATION PROVISION SYSTEM, INFORMATION PROVISION METHOD, PROGRAM, AND SERVER DEVICE

(75) Inventors: Koji Katsuki, Kyoto (JP); Go Shionoya, Kyoto (JP); Yasuhide Kusaka, Kyoto (JP); Yosuke Murase, Kyoto (JP)

(73) Assignee: ARKRAY, Inc., Kyoto (JP)

(*) Notice: Subject to any disclaimer, the term of this patent is extended or adjusted under 35 U.S.C. 154(b) by 0 days.

(21) Appl. No.: 13/259,950

(22) PCT Filed: Apr. 9, 2010

(86) PCT No.: PCT/JP2010/056471
§ 371 (c)(1),
(2), (4) Date: Oct. 14, 2011

(87) PCT Pub. No.: WO2010/119824
PCT Pub. Date: Oct. 21, 2010

(65) Prior Publication Data
US 2012/0110054 A1    May 3, 2012

(30) Foreign Application Priority Data

Apr. 17, 2009  (JP) ................................. 2009-101290
Apr. 17, 2009  (JP) ................................. 2009-101291
Jan. 19, 2010  (JP) ................................. 2010-009474

(51) Int. Cl.
*G06F 15/16*  (2006.01)
(52) U.S. Cl.
USPC ....................... 709/203; 340/539.12; 382/115
(58) Field of Classification Search
None
See application file for complete search history.

(56) References Cited

U.S. PATENT DOCUMENTS 6,206,829 B1 * 3/2001 Iliff .............................. 600/300
6,221,009 B1   4/2001 Doi et al. ..................... 600/300
(Continued)

FOREIGN PATENT DOCUMENTS

EP    2 138 094 A1    12/2009    ............... A61B 5/00
JP    2003-044584     2/2003    .............. G06F 17/60
(Continued)

OTHER PUBLICATIONS

International Search Report for PCT/JP2010/056471 (mailed Jul. 13, 2010).
(Continued)

Primary Examiner — Ninos Donabed
(74) Attorney, Agent, or Firm — Morgan, Lewis & Bockius LLP

(57) ABSTRACT

When continuous user biometric information is transmitted to a server device continuously from a handheld device used by a user, the server device can be caused to receive a required measurement value efficiently at a required time, select information desired by the user on the basis of the measurement value and user peripheral information, and provide the user with the information reliably, without imposing excessive communication charges and the like. A server device 140 is used together with a handheld device 110 that transmits the user peripheral information to the server device and receives the information transmitted from the server device. After determining that a fluctuation has occurred in the user peripheral information transmitted from the handheld device 110, the server device 140 performs either processing for calculating a predicted value of future user biometric information or processing for receiving the predicted value of the future user biometric information, selects information on the basis of the predicted value and the user peripheral information, and transmits the selected information to the handheld device 110.

12 Claims, 23 Drawing Sheets

(56) References Cited

U.S. PATENT DOCUMENTS

| | | | |
|---|---|---|---|
| 6,269,314 B1 | 7/2001 | Iitawaki et al. | 702/23 |
| 6,475,161 B2* | 11/2002 | Teicher et al. | 600/558 |
| 6,478,736 B1 | 11/2002 | Mault | 600/300 |
| 6,612,986 B2 | 9/2003 | Doi et al. | 600/300 |
| 6,790,178 B1 | 9/2004 | Mault et al. | 600/300 |
| 7,126,467 B2* | 10/2006 | Albert et al. | 340/521 |
| 7,188,034 B2 | 3/2007 | Staib et al. | 702/22 |
| 7,535,358 B2* | 5/2009 | Crider et al. | 340/572.1 |
| 7,556,613 B2 | 7/2009 | Wittmann et al. | 604/65 |
| 7,558,622 B2* | 7/2009 | Tran | 600/509 |
| 7,650,244 B2 | 1/2010 | Staib et al. | 702/22 |
| 7,695,677 B2 | 4/2010 | Werner et al. | 422/61 |
| 7,806,853 B2 | 10/2010 | Wittmann et al. | 604/65 |
| 7,878,975 B2 | 2/2011 | Liljeryd et al. | 600/345 |
| 8,108,036 B2* | 1/2012 | Tran | 600/509 |
| 8,344,847 B2* | 1/2013 | Moberg et al. | 340/3.2 |
| 2002/0019752 A1 | 2/2002 | Takase | 705/3 |
| 2002/0062069 A1 | 5/2002 | Mault | 600/300 |
| 2002/0107433 A1 | 8/2002 | Mault | 600/300 |
| 2003/0032077 A1 | 2/2003 | Itoh et al. | 435/14 |
| 2003/0083556 A1* | 5/2003 | Cosentino et al. | 600/300 |
| 2004/0039263 A1* | 2/2004 | Bardy | 600/300 |
| 2004/0039265 A1* | 2/2004 | Bardy | 600/300 |
| 2004/0102683 A1* | 5/2004 | Khanuja et al. | 600/300 |
| 2004/0147982 A1* | 7/2004 | Bardy | 607/60 |
| 2004/0152993 A1* | 8/2004 | Bardy | 600/518 |
| 2004/0153585 A1 | 8/2004 | Kawatahara et al. | 710/52 |
| 2005/0177398 A1 | 8/2005 | Watanabe et al. | 705/3 |
| 2005/0177400 A1* | 8/2005 | Rosenfeld et al. | 705/3 |
| 2005/0182306 A1* | 8/2005 | Sloan | 600/300 |
| 2005/0191716 A1* | 9/2005 | Surwit et al. | 435/13 |
| 2005/0228300 A1* | 10/2005 | Jaime et al. | 600/485 |
| 2005/0240611 A1 | 10/2005 | Itoh et al. | 707/101 |
| 2006/0071797 A1* | 4/2006 | Rosenfeld et al. | 340/573.1 |
| 2006/0085229 A9* | 4/2006 | Rosenfeld et al. | 705/3 |
| 2006/0136513 A1* | 6/2006 | Ngo et al. | 707/203 |
| 2006/0206011 A1* | 9/2006 | Higgins et al. | 600/300 |
| 2006/0293571 A1* | 12/2006 | Bao et al. | 600/300 |
| 2007/0148778 A1 | 6/2007 | Staib et al. | 436/63 |
| 2007/0276270 A1* | 11/2007 | Tran | 600/508 |
| 2008/0092638 A1 | 4/2008 | Brenneman et al. | 73/61.41 |
| 2008/0114215 A1 | 5/2008 | Ward et al. | 600/300 |
| 2008/0234992 A1 | 9/2008 | Ray et al. | 703/2 |
| 2008/0235053 A1 | 9/2008 | Ray et al. | 705/3 |
| 2009/0054735 A1* | 2/2009 | Higgins et al. | 600/300 |
| 2009/0318779 A1* | 12/2009 | Tran | 600/301 |
| 2010/0152549 A1 | 6/2010 | Tamura | 600/301 |
| 2011/0166791 A1 | 7/2011 | Liljeryd et al. | 702/19 |
| 2011/0231296 A1* | 9/2011 | Gross et al. | 705/37 |

FOREIGN PATENT DOCUMENTS

| | | | |
|---|---|---|---|
| JP | 2003-57244 | 2/2003 | G06Q 33/66 |
| JP | 2003-173375 | 6/2003 | G06F 17/60 |
| JP | 2005-267364 | 9/2005 | G06F 17/60 |
| JP | 2005-328924 | 12/2005 | A61B 5/145 |
| JP | 2006-099301 | 4/2006 | G06Q 50/00 |
| JP | 2006-163859 | 6/2006 | G06Q 50/00 |
| JP | 2008-167829 | 7/2008 | A61B 5/157 |
| WO | WO 2008/136050 | 11/2008 | A61B 5/00 |

OTHER PUBLICATIONS

English translation of International Preliminary Report on Patentability issued in the corresponding PCT Application No. PCT/JP2010/056471, dated Dec. 1, 2011.

Extended European Search Report issued in counterpart European Patent Application No. 10764408.0 dated Apr. 11, 2014.

* cited by examiner

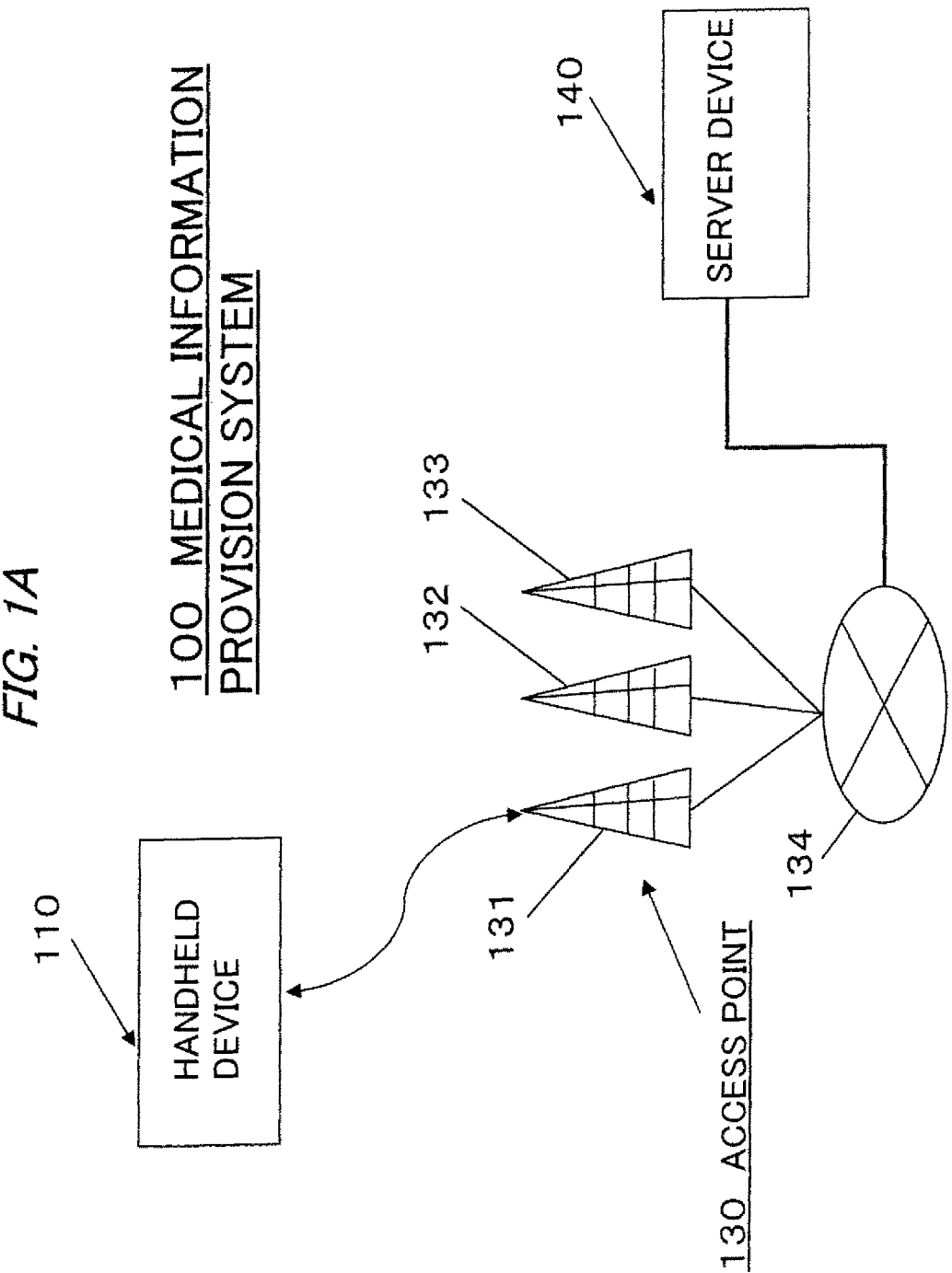

FIG. 2A

DATA RECORD STORED IN USER-SPECIFIC INFORMATION STORAGE UNIT 125 OF HANDHELD DEVICE 110

| USER IDENTIFICATION INFORMATION | UPDATE DATE AND TIME | USER-SPECIFIC INFORMATION | | | | | | |
|---|---|---|---|---|---|---|---|---|
| | | EATING | | SLEEP | | EXERCISE | | |
| | | EATING START TIME | CARBOHYDRATE INTAKE | BEDTIME | HOURS OF SLEEP | EXERCISE START TIME | DURATION OF EXERCISE | |
| 0000AA1 | 2009/8/21 16:00 | 7:30 | 250g | 23:00 | 6.0 HOURS | 16:00 | 1.0 HOUR | |

| USER-SPECIFIC INFORMATION | | | | | |
|---|---|---|---|---|---|
| BATHING | | | MEDICINE (INSULIN) ADMINISTRATION | | |
| BATH START TIME | DURATION OF BATH | | ADMINISTRATION TIME | DOSAGE | |
| 21:30 | 15 MINUTES | | 8:00 | 17G | |

FIG. 2B

DATABASE STORED IN ACCESS POINT INFORMATION STORAGE UNIT 152 OF SERVER DEVICE 140

| USER IDENTIFICATION INFORMATION | UPDATE DATE AND TIME | ACCESS POINT INFORMATION |
|---|---|---|
| 0000AA1 | 2009/8/21 16:00 | A |
| 0000AA2 | 2009/8/21 16:00 | B |
| 0000AA3 | 2009/8/21 16:00 | B |
| 0000AA4 | 2009/8/21 16:00 | C |
| 0000AA5 | 2009/8/21 16:00 | C |

FIG. 2C

DATABASE STORED IN USER-SPECIFIC INFORMATION STORAGE UNIT 150 OF SERVER DEVICE 140

| USER IDENTIFICATION INFORMATION | UPDATE DATE AND TIME | USER-SPECIFIC INFORMATION | | | | | | |
|---|---|---|---|---|---|---|---|---|
| | | EATING | | SLEEP | | EXERCISE | | |
| | | EATING START TIME | CARBOHYDRATE INTAKE | BEDTIME | HOURS OF SLEEP | EXERCISE START TIME | DURATION OF EXERCISE | |
| 0000AA1 | 2009/8/21 16:00 | 7:30 | 250g | 23:00 | 6.0 HOURS | 16:00 | 1.0 HOUR | |
| 0000AA2 | 2009/8/21 16:00 | 8:00 | 100g | 23:00 | 6.0 HOURS | 7:45 | 0.5 HOUR | |
| 0000AA2 | 2009/8/21 16:00 | 8:15 | 300g | 0:00 | 6.0 HOURS | 7:00 | 0.5 HOUR | |

| USER-SPECIFIC INFORMATION | | | |
|---|---|---|---|
| BATHING | | MEDICINE (INSULIN) ADMINISTRATION | |
| BATH START TIME | DURATION OF BATH | ADMINISTRATION TIME | DOSAGE |
| 21:30 | 15 MINUTES | 8:00 | 17G |
| 23:30 | 30 MINUTES | 8:30 | 21G |
| 19:00 | 20 MINUTES | 8:45 | 30G |

FIG. 2D

DATABASE STORED IN PROFILE GENERATION STORAGE UNIT 153 OF SERVER DEVICE 140

| FLUCTUATION PATTERN OF PAST BIOMETRIC INFORMATION | BLOOD SUGAR LEVEL DATA SEQUENCE SAMPLES CORRESPONDING TO EACH PATTERN | FLUCTUATION VALUE (mg/dl) OF FUTURE BLOOD SUGAR LEVEL FROM PAST TIME P |
|---|---|---|
| PATTERN 1 | SINGLE BLOOD SUGAR LEVEL DATA SEQUENCE SAMPLE 1, SINGLE BLOOD SUGAR LEVEL DATA SEQUENCE SAMPLE 16, SINGLE BLOOD SUGAR LEVEL DATA SEQUENCE SAMPLE 10, ... | -15.6 |
| PATTERN 2 | SINGLE BLOOD SUGAR LEVEL DATA SEQUENCE SAMPLE 8, SINGLE BLOOD SUGAR LEVEL DATA SEQUENCE SAMPLE 4, SINGLE BLOOD SUGAR LEVEL DATA SEQUENCE SAMPLE 14, ... | 26.5 |
| PATTERN 3 | SINGLE BLOOD SUGAR LEVEL DATA SEQUENCE SAMPLE 18, SINGLE BLOOD SUGAR LEVEL DATA SEQUENCE SAMPLE 17, SINGLE BLOOD SUGAR LEVEL DATA SEQUENCE SAMPLE 3, ... | -9.65 |
| PATTERN 4 | SINGLE BLOOD SUGAR LEVEL DATA SEQUENCE SAMPLE 5, SINGLE BLOOD SUGAR LEVEL DATA SEQUENCE SAMPLE 12, SINGLE BLOOD SUGAR LEVEL DATA SEQUENCE SAMPLE 9, ... | 22.4 |
| PATTERN 5 | SINGLE BLOOD SUGAR LEVEL DATA SEQUENCE SAMPLE 8, SINGLE BLOOD SUGAR LEVEL DATA SEQUENCE SAMPLE 4, SINGLE BLOOD SUGAR LEVEL DATA SEQUENCE SAMPLE 14, ... | 24 |
| PATTERN 6 | SINGLE BLOOD SUGAR LEVEL DATA SEQUENCE SAMPLE 18, SINGLE BLOOD SUGAR LEVEL DATA SEQUENCE SAMPLE 17, SINGLE BLOOD SUGAR LEVEL DATA SEQUENCE SAMPLE 3, ... | -12.5 |

FIG. 2E

DATABASE STORED IN USER BIOMETRIC INFORMATION STORAGE UNIT 151 OF SERVER DEVICE 140

| USER IDENTIFICATION INFORMATION | UPDATE DATE AND TIME | USER BIOMETRIC INFORMATION |
|---|---|---|
| 0000AA1 | 2009/8/21 16:00 | 120 |
| 0000AA2 | 2009/8/21 16:00 | 100 |
| 0000AA3 | 2009/8/21 16:00 | 80 |
| 0000AA4 | 2009/8/21 16:00 | 150 |
| 0000AA5 | 2009/8/21 16:00 | 154 |

FIG. 2F

DATABASE STORED IN ACCESS POINT AREA INFORMATION STORAGE UNIT 154 OF SERVER DEVICE 140

| ACCESS POINT INFORMATION | INFORMATION INDICATING MEDICAL INSTITUTIONS BELONGING TO AREA | TODAY'S WEATHER | INFORMATION INDICATING DRUGSTORES BELONG TO AREA |
|---|---|---|---|
| A | MEDICAL INSTITUTION (1), MEDICAL INSTITUTION (2), MEDICAL INSTITUTION (3) | FINE | DRUGSTORE A |
| B | MEDICAL INSTITUTION (4), MEDICAL INSTITUTION (5) | FINE, OCCASIONALLY CLOUDY | DRUGSTORE B, PHARMACY A |
| C | MEDICAL INSTITUTION (6), MEDICAL INSTITUTION (7), MEDICAL INSTITUTION (8) | RAIN | DRUGSTORE C, PHARMACY B, PHARMACY C |

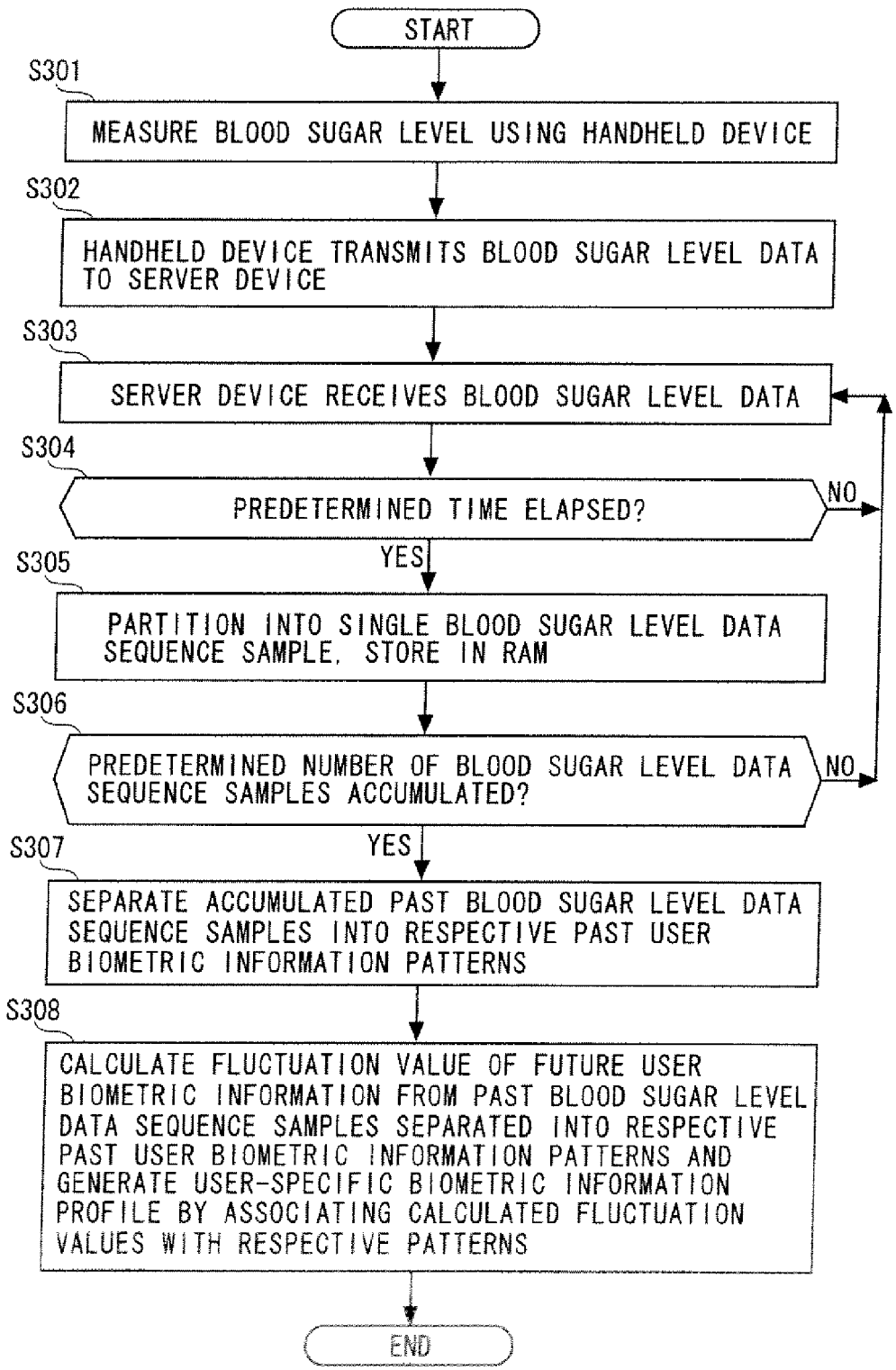

FIG. 5

EXAMPLES OF FLUCTUATION PATTERNS OF PAST BIOLOGICAL INFORMATION

| | DIVERGENCE RATE | RATE OF CHANGE | DIFFERENCE |
|---|---|---|---|
| PATTERN 1 | POSITIVE | POSITIVE | POSITIVE |
| PATTERN 2 | POSITIVE | POSITIVE | NEGATIVE |
| PATTERN 3 | POSITIVE | NEGATIVE | POSITIVE |
| PATTERN 4 | NEGATIVE | POSITIVE | POSITIVE |
| PATTERN 5 | POSITIVE | NEGATIVE | POSITIVE |
| PATTERN 6 | NEGATIVE | NEGATIVE | NEGATIVE |

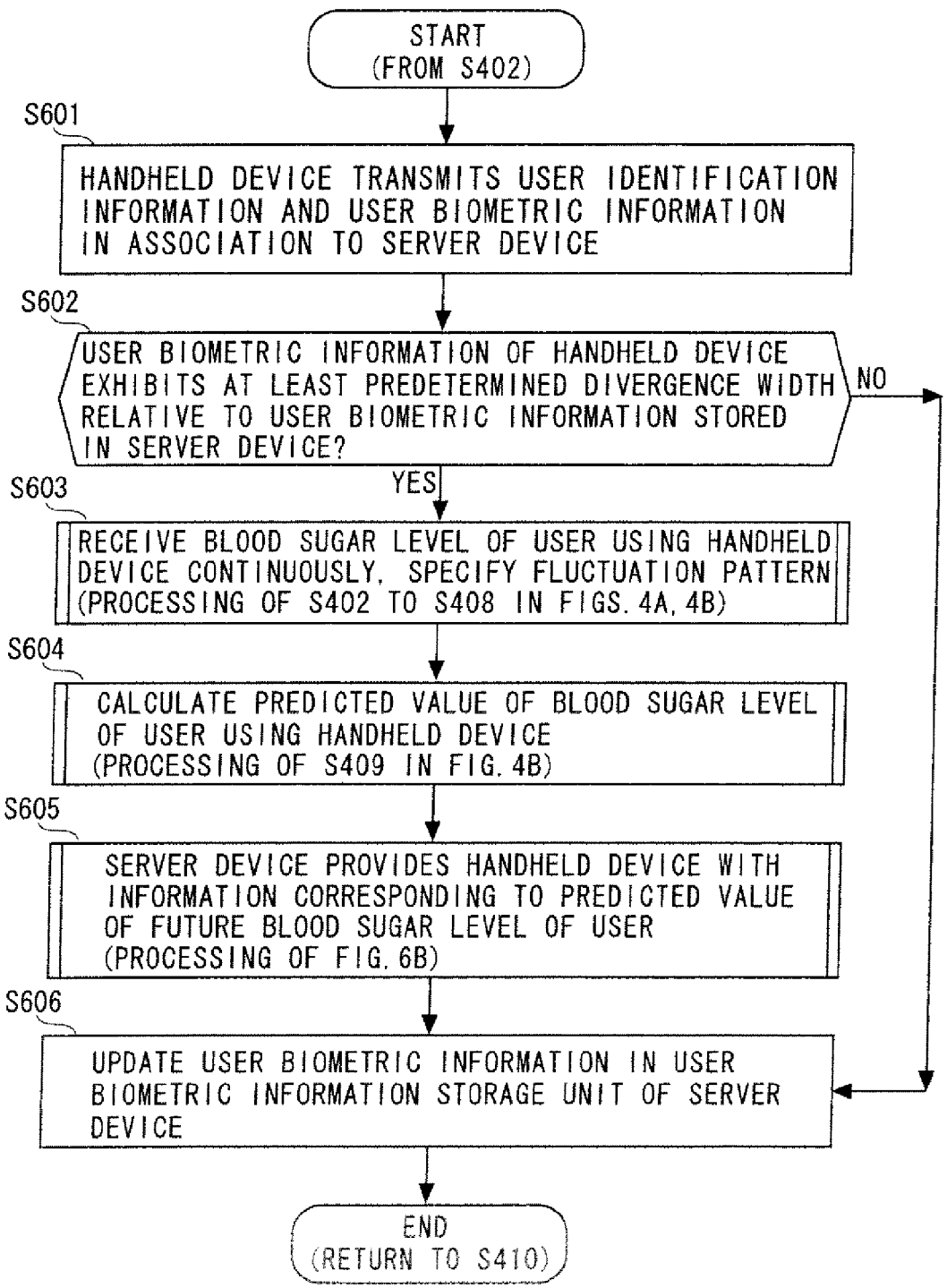

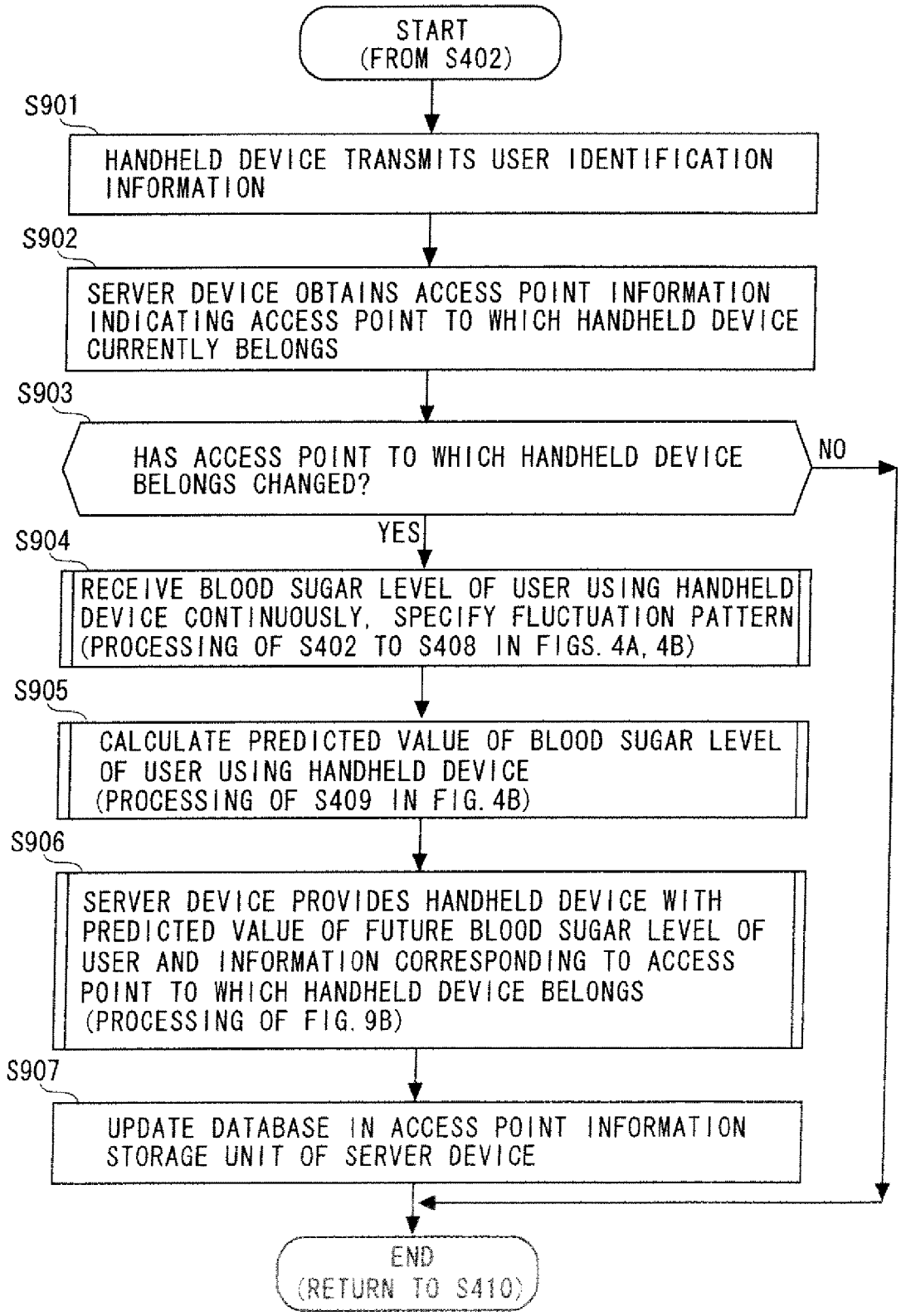

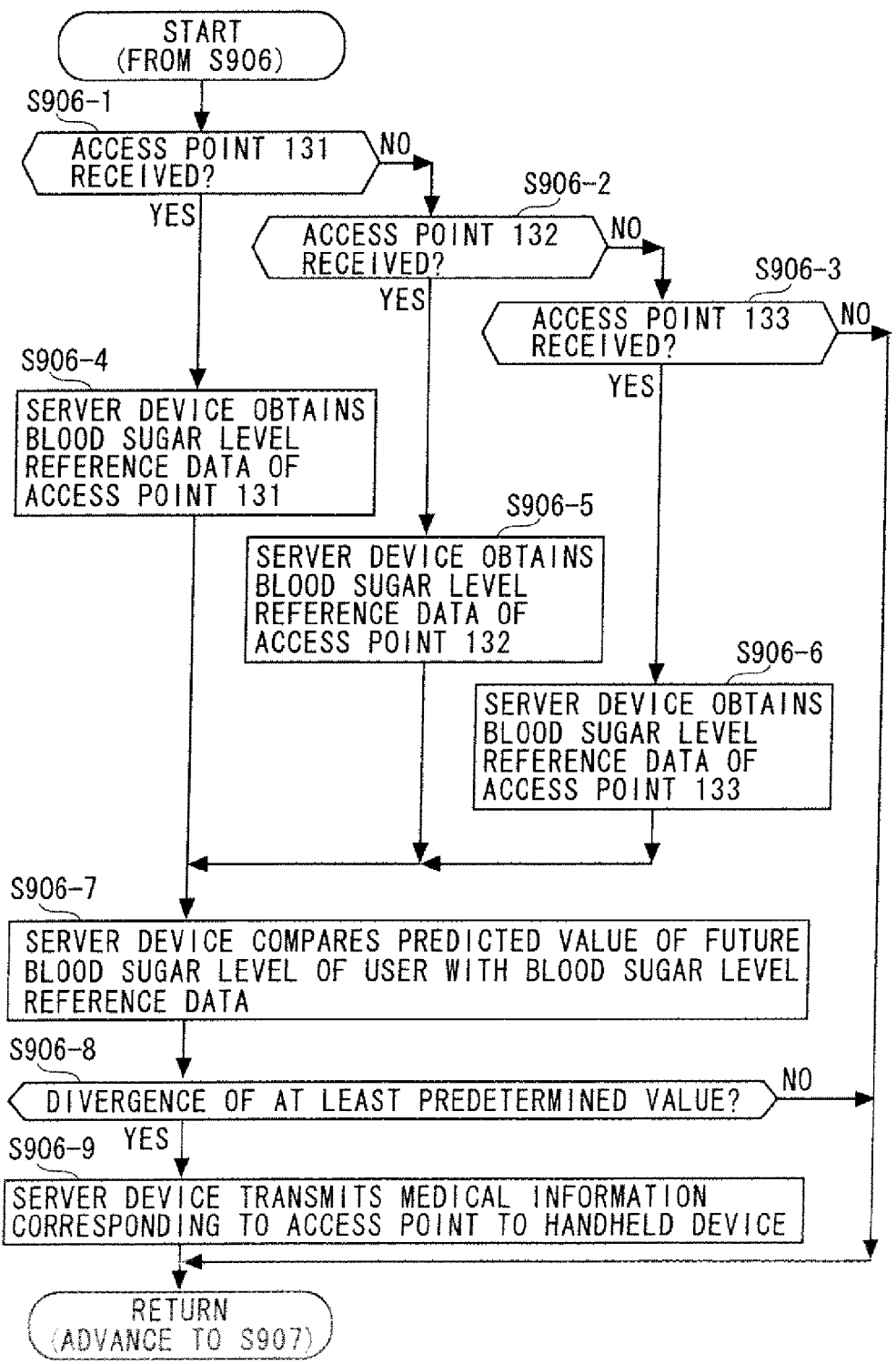

FIG. 10

| | SIGN OF DIVERGENCE | DEGREE OF DIVERGENCE | TRANSMITTED MEDICAL INFORMATION |
|---|---|---|---|
| UNIQUE MEDICAL INFORMATION CORRESPONDING TO ACCESS POINT 131 | POSITIVE | SMALL | EAT A MEAL LOW IN SUGAR TO PREVENT HIGH BLOOD SUGAR |
| | POSITIVE | MEDIUM | TALK TO YOUR DOCTOR ABOUT YOUR INSULIN ADMINISTRATION |
| | POSITIVE | LARGE | GO TO A MUNICIPAL HOSPITAL |
| | NEGATIVE | SMALL | EAT A MEAL CONTAINING SUGAR TO PREVENT LOW BLOOD SUGAR |
| | NEGATIVE | MEDIUM | EAT A MEAL CONTAINING SUFFICIENT SUGAR |
| | NEGATIVE | LARGE | GO TO A TOWN HOSPITAL |
| UNIQUE MEDICAL INFORMATION CORRESPONDING TO ACCESS POINT 132 | POSITIVE | SMALL | EAT A MEAL LOW IN SUGAR TO PREVENT HIGH BLOOD SUGAR |
| | POSITIVE | MEDIUM | TALK TO YOUR DOCTOR ABOUT YOUR INSULIN ADMINISTRATION AND TAKE APPROPRIATE EXERCISE |
| | POSITIVE | LARGE | GO TO B MUNICIPAL HOSPITAL |
| | NEGATIVE | SMALL | EAT A MEAL CONTAINING SUGAR TO PREVENT LOW BLOOD SUGAR |
| | NEGATIVE | MEDIUM | REPLENISH YOUR SUGAR AND TAKE APPROPRIATE EXERCISE |
| | NEGATIVE | LARGE | GO TO B MEMORIAL HOSPITAL |
| UNIQUE MEDICAL INFORMATION CORRESPONDING TO ACCESS POINT 133 | POSITIVE | SMALL | EAT A MEAL LOW IN SUGAR TO PREVENT HIGH BLOOD SUGAR |
| | POSITIVE | MEDIUM | TALK TO YOUR DOCTOR ABOUT YOUR INSULIN ADMINISTRATION AND MAKE SURE YOU GET ENOUGH SLEEP |
| | POSITIVE | LARGE | GO TO C MEMORIAL HOSPITAL |
| | NEGATIVE | SMALL | EAT A MEAL CONTAINING SUGAR TO PREVENT LOW BLOOD SUGAR |
| | NEGATIVE | MEDIUM | REPLENISH YOUR SUGAR AND MAKE SURE YOU GET ENOUGH SLEEP |
| | NEGATIVE | LARGE | GO TO C MUNICIPAL HOSPITAL |

INFORMATION PROVISION SYSTEM, INFORMATION PROVISION METHOD, PROGRAM, AND SERVER DEVICE

CROSS-REFERENCE TO RELATED APPLICATIONS

This application is the U.S. National Phase under 35 U.S.C. §371 of International Application PCT/JP2010/056471, filed Apr. 9, 2010, which was published in a non-English language, which claims priority to JP Application No. 2009-101291, filed Apr. 17, 2009, JP Application No. 2009-101290, filed Apr. 17, 2009 and JP Application No. 2010-009474, filed Jan. 19, 2010, which are hereby incorporated by reference in their entirety.

TECHNICAL FIELD

The present invention relates to an information provision system, an information provision method, a program, a server device, and a handheld device for providing information while managing a condition of a user.

BACKGROUND OF THE INVENTION

A medical service employed in a handheld measuring instrument (a handheld device), for example, in which data are transmitted using a portable telephone, has been proposed in the related art of the medical field (see Patent Document 1, for example).

Further, a system in which blood sugar level information transmitted from a handheld blood sugar measuring instrument is received via an access point, the received blood sugar information is managed by a server, and when an abnormality is detected in the blood sugar condition, the server provides a user with appropriate information has been proposed (see Patent Document 2, for example).

Patent document 1: Japanese Patent Application Publication No. 2002-368904
Patent document 2: Japanese Patent Application Publication No. 2003-057244
Patent document 3: Japanese Patent Application Publication No. 2005-308742

SUMMARY OF THE INVENTION

However, when continuous user biometric information, for example information obtained by measuring measurement values continuously over time, is received by a server from a handheld measuring instrument (a handheld device) used by a user and managed by the server continuously, the amount of information is excessively large, and as a result, a large load is exerted on a communication facility, leading to a system error (a bug). In a case where the server receives the continuously obtained measurement values in real time via the communication facility during an emergency and information of some kind must be transmitted from the server to the handheld device immediately on the basis of the measurement values, the system error is particularly likely to occur, and in such situations it is difficult to provide the user with the information reliably from the server. As a result, appropriate treatment and medicine may not be administered, potentially endangering the life of the user.

Furthermore, even if predetermined measurement values can be received continuously in a server device, when the amount of information, including the continuously obtained measurement values and so on, becomes excessively large, excessive communication charges and so on are imposed on the user. It is therefore desirable to enable the server to receive only required measurement values efficiently at a required time and provide the user with information desired by the user reliably on the basis of the measurement values.

It is also desirable for the server to select information required by the user and provide the user with the selected information not only during an emergency, but also in accordance with a fluctuation in user peripheral information that affects the continuous user biometric information, for example variation in events occurring during everyday life such as eating, sleep, bathing, exercise, and medicine administration, or variation in dietary habits and environmental variation such as climate variation occurring when the user moves to another area. By providing this information, the user can predict dangers to his/her life before they arise and forestall the dangers by taking countermeasures.

The present invention has been designed in consideration of these problems, and an object thereof is to ensure that a server receives only a required amount of information from a handheld device at a required time, and that the server selects information required by a user and provides the information reliably.

To achieve the object, an information provision system according to the present invention includes a handheld device that transmits user peripheral information to a server device and receives information transmitted from the server device, and the server device, wherein the server device either performs processing for receiving continuous user biometric information obtained by measuring user biometric information continuously from the handheld device and calculating a predicted value of future user biometric information from the received continuous user biometric information after determining that a fluctuation has occurred in the user peripheral information, or performs processing for receiving the predicted value of the future user biometric information from the handheld device after determining theta fluctuation has occurred in the user peripheral information, and on the basis of the predicted value of the future user biometric information and the user peripheral information, the server device selects information and transmits the selected information to the handheld device.

Further, to achieve the object, an information provision method according to the present invention uses a handheld device that transmits user peripheral information to a server device and receives information transmitted from the server device, and the server device, wherein the server device executes the steps of: determining whether or not a fluctuation has occurred in the user peripheral information; either receiving continuous user biometric information obtained by measuring user biometric information continuously from the handheld device and calculating a predicted value of future user biometric information from the continuous user biometric information after determining that a fluctuation has occurred in the user peripheral information or receiving the predicted value of the future user biometric information from the handheld device after determining that a fluctuation has occurred in the user peripheral information; selecting Information on the basis of the predicted value of the future user biometric information and the user peripheral information; and transmitting the selected information to the handheld device.

Further, to achieve the object, a program according to the present invention causes a computer to execute: processing for receiving user peripheral information transmitted from a handheld device; processing for determining whether or not a fluctuation has occurred in the user peripheral information;

either processing for receiving continuous user biometric information obtained by measuring user biometric information continuously from the handheld device and calculating a predicted value of future user biometric information from the received continuous user biometric information after determining that a fluctuation has occurred in the user peripheral information, or processing for transmitting an instruction signal for instructing the handheld device to calculate the predicted value of the future user biometric information from the continuous user biometric information and transmit the predicted value of the future user biometric information, to the handheld device and receiving the predicted value of the future user biometric information transmitted from the handheld device on the basis of the instruction signal after determining that a fluctuation has occurred in the user peripheral information; processing for selecting information on the basis of the predicted value of the future user biometric information and the user peripheral information; and processing for transmitting the selected information to the handheld device.

Further, to achieve the object, a server device according to the present invention, which receives user peripheral information transmitted from a handheld device and transmits information to the handheld device, includes a determination unit for determining whether or not a fluctuation has occurred in the user peripheral information, wherein the determination unit either performs processing for receiving continuous user biometric information obtained by measuring user biometric information continuously from the handheld device and calculating a predicted value of future user biometric information from the received continuous user biometric information after determining that a fluctuation has occurred in the user peripheral information, or performs processing for receiving the predicted value of the future user biometric information from the handheld device after determining that a fluctuation has occurred in the user peripheral information, and on the basis of the predicted value of the future user biometric information and the user peripheral information, the determination unit selects information and transmits the selected information to the handheld device.

As described above, with the information provision system, information provision method, program, server device, and handheld device according to the present invention, the server device can receive required continuous user biometric information at a required time not only during an emergency, but also in accordance with a fluctuation in user peripheral information that affects the continuous user biometric information, for example variation in events occurring during everyday life such as eating, sleep, bathing, exercise, and medicine administration, or variation in dietary habits and environmental variation such as climate variation accompanying a move to another area, and the server device can select information desired by a user on the basis of this information and provide the user with the information reliably.

BRIEF DESCRIPTION OF THE DRAWINGS

FIG. 1A is a block diagram showing the overall constitution of an information provision system 100 according to an embodiment of the present invention.

FIG. 2A is a view showing a data record stored in respective auxiliary storage units of the handheld device and the server device.

FIG. 2B is a view showing a database stored in the respective auxiliary storage units of the handheld device and the server device.

FIG. 2C is a view showing a database stored in the respective auxiliary storage units of the handheld device and the server device.

FIG. 2D is a view showing a database stored in the respective auxiliary storage units of the handheld device and the server device.

FIG. 2E is a view showing a database stored in the respective auxiliary storage units of the handheld device and the server device.

FIG. 2F is a view showing a database stored in the respective auxiliary storage units of the handheld device and the server device.

FIG. 3 is a flowchart showing biometric information profile generation processing for generating a user-specific biometric information profile.

FIG. 5 is a view showing examples of fluctuation patterns (pattern 1 to pattern 6) in past biometric information.

FIG. 6A is a flowchart showing processing in which user biometric information is used as the user peripheral information, the server device determines whether or not a fluctuation has occurred therein, and when a fluctuation is acknowledged, required information is selected from this information and the predicted value of the future user biometric information and provided to the handheld device of the user.

FIG. 9A is a flowchart showing processing for selecting the required information and providing the handheld device of the user therewith.

FIG. 9B is a flowchart showing processing for selecting the required information and providing the handheld device of the user therewith.

FIG. 10 is a view showing an example of a medical information table.

DETAILED DESCRIPTION OF THE INVENTION

Embodiment

An embodiment of the present invention will be described in detail below with reference to the drawings.

In this embodiment, a case in which a blood sugar level is measured continuously as continuous user biometric information will be described as an example. However, the present invention is not limited to the blood sugar level, and the measured biometric information may also be GOT, OPT, LOH, γ-GT, alkaline phosphatase, choline esterase, lipase, creatinine kinase, ammonia, cholesterol level, blood pressure, body temperature, body fat percentage, pulse, and so on. Further, the measurement subject is not limited to blood and may be blood serum, plasma, interstitial fluid, and so on.

Further, as will be described below, the continuous user biometric information is a series of information obtained by converting signals taken continuously over time in a measurement unit into values expressing the measured biometric information, associating times at which the signals were taken with the values expressing the measured biometric information, and arranging the resulting information continuously with respect to time. Moreover, user biometric information is partial information included in the continuous user biometric information, which is obtained by partitioning the values expressing the continuously arranged measured biometric information relative to time. Hence, the number of values expressing the biometric information included in the user biometric information is smaller than the number of values in the continuous user biometric information.

Furthermore, user peripheral information is information that affects the continuous user biometric information in some way, for example events occurring during everyday life such as eating, sleep, bathing, exercise, and medicine administration, or variation in dietary habits and environmental variation such as climate variation accompanying a move to another area. However, the user peripheral information is not limited thereto.

Figure 1B:
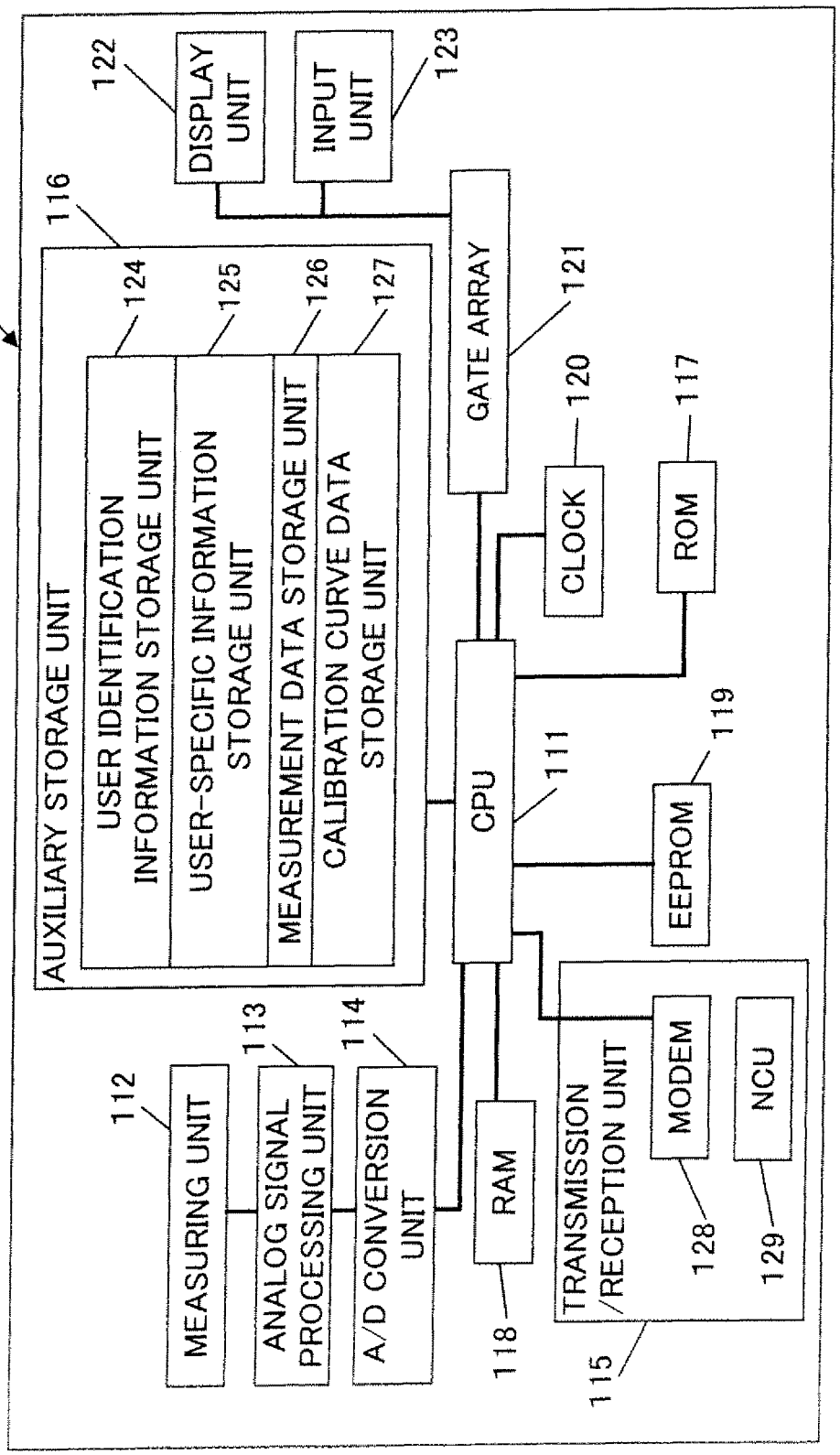
FIG. 1B is an illustrative view of a handheld device 110 according to an embodiment of the present invention.
Figure 1C:
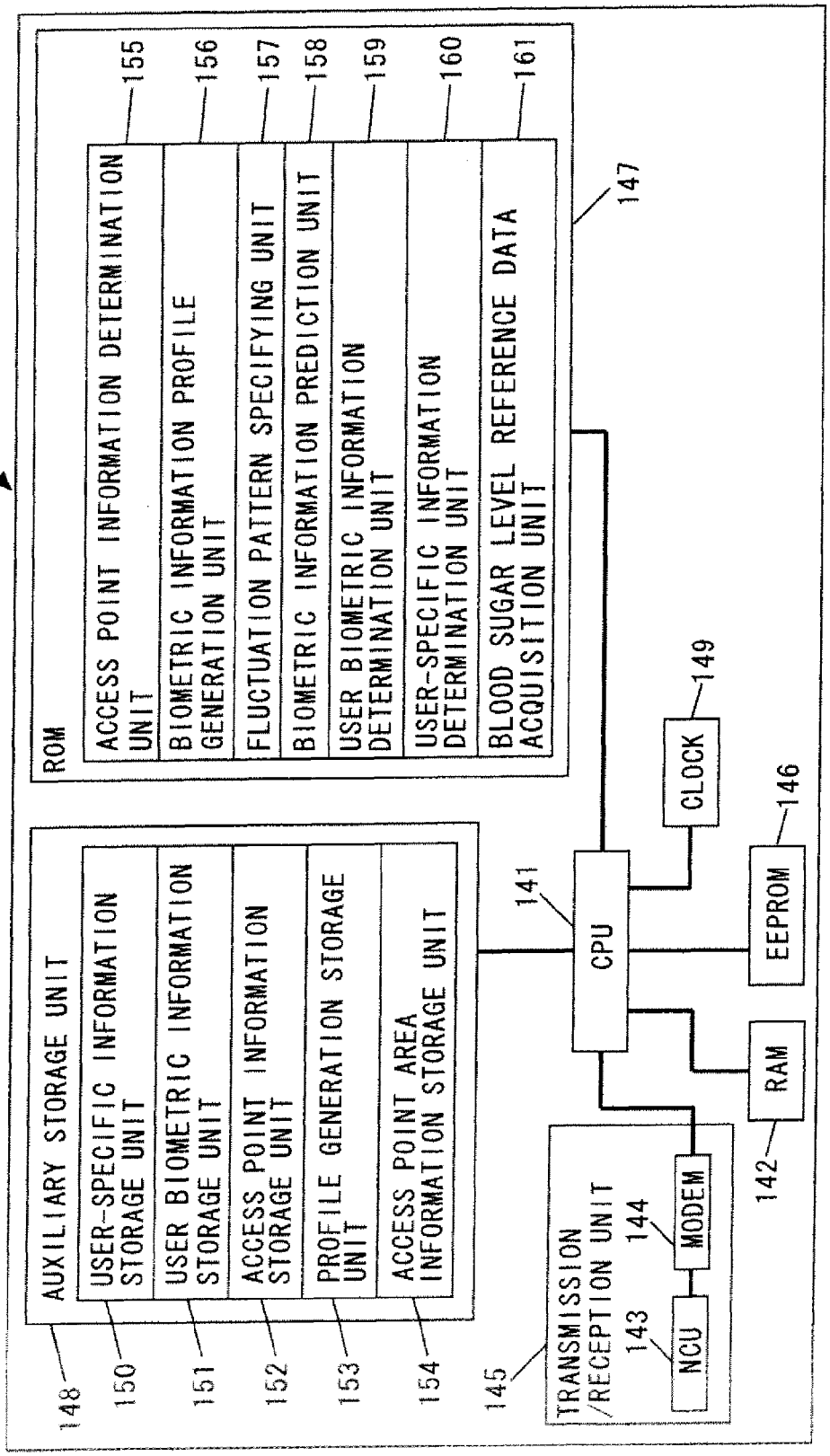
FIG. 1C is an illustrative view of a server device 140 according to an embodiment of the present invention.

FIG. 1A is a block diagram showing the overall constitution of an information provision system 100 according to an embodiment of the present invention. The user-specific information provision system 100 is constituted by a handheld device 110, access points 130, and a server device 140. FIG. 13 is an illustrative view of the handheld device 110 according to this embodiment of the present invention. FIG. 1C is an illustrative view of the server device 140 according to this embodiment of the present invention. Constitutions and features of the respective devices will be described below.

The access points 130 are constituted by access points 131, 132 and 133. The access points 131, 132, 133 are disposed in respective areas and respectively define ranges (areas) in which communication is possible with the handheld device 110. The handheld device 110 and the server device 140, to be described below, are connected via a single access point (the access point 131 in FIG. 1). The access points 130 and the handheld device 110 may be connected wirelessly or through a wire. When the handheld device 110 is in a range enabling communication with the access point 131, the handheld device is assumed to belong to the access point. The access points 130 and the server device 140 may be connected either directly or via a communication network 134 (a telephone network, the Internet, a satellite network, and so on). The access points 130 are provided with an information attachment unit for attaching access point information to information transmitted via the access points 130 so that the access point information is associated with the transmitted information. The access point information is information enabling identification of the individual access points, for example a number, a code, or the like. The access points 130 receive blood sugar level data transmitted from the handheld device 110. Note that FIG. 1 shows three access points, namely the access point 131, the access point 132, and the access point 133, but the number of access points is not limited to three and may be another plurality.

The handheld device 110 is configured as a computer, as described below. The handheld device 110 includes a CPU 111 that performs overall control of the handheld device 110, and the CPU 111 executes various processing in accordance with instructions from various programs stored in a RAM 118. A measuring unit 112, an analog signal processing unit 113 that amplifies an output signal from the measuring unit 112, an A/D conversion unit 114 that converts an output signal from the analog signal processing unit into a digital signal, a transmission/reception unit 115 that transmits and receives data to and from the outside, an auxiliary storage unit 116, a ROM 117 storing various programs, the RAM 118 for storing various data and so on processed by the CPU 111 and the programs stored in the ROM 117, an EEPROM 119 storing flags and so on, a clock 120, a gate array 121 that controls input/output (a display unit 122, an input unit 123) to and from the CPU 111, and the display unit 122 and input unit 123 connected to the gate array are connected to the CPU 111 by a bus line. Further, the auxiliary storage unit 116 is constituted by a user identification information storage unit 124, a user-specific information storage unit 125, a measurement data storage unit 126, and a calibration curve data storage unit 127. A hard disk, a flash memory, or the like is used as the auxiliary storage unit 116, but the auxiliary storage unit 116 is not limited thereto. Note that the handheld device 110 is preferably formed to be portable by a single user but is not limited thereto. The measuring unit 112 extracts a fluctuation in the body of the user continuously in the form of signals. For example, a measuring instrument described in Japanese National Publication of International Patent Application No. 2004-520898, in which signals representing blood sugar levels are taken continuously by inserting a blood sugar level sensor into the skin of an arm portion, an abdomen portion, or the like of the body of a user via an insertion needle, is used. A signal expressing a fluctuation in the body of the user, output from the measuring unit 112, is amplified by the analog signal processing unit, converted into a digital signal by the A/D conversion unit 114, and transmitted to the CPU 111. The CPU 111 converts the output signal into a component concentration by referring to the calibration curve data stored in the calibration curve data storage unit 127 of the auxiliary storage unit 116, displays a concentration value on the display unit 122 as measurement data, obtains date and time information from the clock 120, and stores the obtained date and time information and the measurement data in association in the measurement data storage unit 126 as the continuous user biometric information. As described above, signals expressing blood sugar levels are taken continuously by the measuring unit 112, and therefore the continuous user biometric information stored in the measurement data storage unit 126 is likewise stored as continuous data. The transmission/reception unit 115 is connected to a modem 128 and a communication line in order to perform network control. The modem 128 demodulates reception data and modulates transmission data. The user identification information storage unit 124 stores user identification information. The user identification information is information enabling identification of the user of the handheld device or information enabling identification of the handheld device 110 itself, for example an ID number, a passcode, a QR code, a two-dimensional code, a serial number, or the like. Note that means for displaying the user identification information on the handheld device 110 includes displaying the identification information on a display unit and adhering the user identification information to a surface of a housing of the handheld device 110. The user-specific information storage unit 125 is a single record in which the user-specific information is stored in association with the user identification information of the handheld device 110 and an update date and time (the date and time information obtained from the clock). FIG. 2A shows this record. Note that in FIG. 2A, eating (meal time, carbohydrate intake), sleep (bedtime, hours of sleep), bathing (bath start time, duration of bath), exercise (exercise start time, duration of exercise), and medicine (insulin) administration (administration time, dosage), i.e. everyday events during which the blood sugar level of the user is comparatively likely to vary, are listed in each field as the user-specific information, but the user-specific information is not limited thereto, and allergies, past history, chronic diseases, and so on may also be used. The user-specific information may be updated in accordance with the wishes of the user, or the CPU 111 may generate an alarm periodically on the display unit using the time and date information obtained from the clock 120, thereby encouraging the user to perform an update operation. When the user inputs update content pertaining to the respective fields into the input unit in order to update the data, the CPU refers to the respective fields of the user-specific information storage unit 125 and updates the data in accordance with the update content input into the input unit.

The server device 140 is configured as a computer, as described below. The server device 140 includes a CPU 141 that performs overall control of the server device 140, and the CPU 141 executes various processing in accordance with instructions from various programs stored in a RAM 142. A transmission/reception unit 145 constituted by an NCU 143 and a modem 144, an EEPROM 146 storing flags and so on, a ROM 147 storing various programs, the RAM 142 for storing various data and the like processed by the CPU 141 and the programs stored in the ROM 147, an auxiliary storage unit 148, and a clock 149 are connected to the CPU 141 via a bus line. The NCU 143 constituting the transmission/reception unit is connected to the modem 144 and a communication line in order to perform network control. The modem 144 demodulates reception data and modulates transmission data. The auxiliary storage unit 148 is constituted by respective databases of a user-specific information storage unit 150, a user biometric information storage unit 151, an access point information storage unit 152, a profile generation storage unit 153, and an access point area information storage unit 154. A hard disk, a flash memory, or the like is used as the auxiliary storage unit 148, but the auxiliary storage unit 148 is not limited thereto. The access point information storage unit 152 is a database associating the user identification information of individual handheld devices 110, the access point information, and the update time and date (the time and date information obtained from the clock) in order to learn the access point 130 to which each individual handheld device 110 currently belongs. FIG. 2B shows this database. The user-specific information storage unit 150 is a database associating the user identification information of the individual handheld devices 110, the update time and date (the time and date information obtained from the clock), and the user-specific information of the users using the individual handheld devices. FIG. 2C shows this database. The user biometric information storage unit 151 is a database associating the user biometric information of the individual handheld devices 110 with the update time and date (the time and date information obtained from the clock). FIG. 2E shows this database. The access point area information storage unit 154 is a database storing information relating to the areas to which the individual access points belong, or in other words information (here, medical institution information and area information) relating to an area in the communicable range of the access point, in association with the access point information. In FIG. 2F, addresses, contact addresses, map positions, and so on of medical institutions are used as the medical institution information, while daily weather information, drugstore information (addresses, contact addresses, and map positions of drugstores and pharmacies), and so on are used as the area information. However, there are no particular limitations on the information as long as it is unique to the area of the access point, and information describing dietary habits or information describing the typical climate of the area, for example, may also be used. The ROM 147 is constituted by an access point information determination unit 155, a biometric information profile generation unit 156, a fluctuation pattern specifying unit 157, a biometric information prediction unit 158, a user biometric information determination unit 159, and a user-specific information determination unit 160. The biometric information profile generation unit 156 stores a program that enables processing for generating a user-specific biometric information profile on the basis of past user blood sugar level data sequences (past user biometric information of the user transmitted from the handheld device) accumulated over a predetermined period, and storing the user-specific biometric information profile in the profile generation storage unit 153 of the auxiliary storage unit 148 in the form of a database (shown in FIG. 2D). The fluctuation pattern specifying unit 157 stores a program that enables processing for specifying a fluctuation pattern in the past user biometric information that matches a fluctuation pattern in recent user biometric information of the user from the user-specific biometric information profile stored in the profile generation storage unit 153. The biometric information prediction unit 158 stores a program for calculating a predicted value of future user biometric information by adding a fluctuation value of the future user biometric information, which is associated with the fluctuation pattern in the past user biometric information specified by the fluctuation pattern specifying unit 157, to current user biometric information. The user biometric information determination unit 159 stores a program for determining whether or not a divergence of at least a predetermined width exists between the user biometric information of the handheld device 110 and the user biometric information stored in the user biometric information storage unit 151 of the server device 140 and, when the divergence of at least the predetermined width exists, executing the programs stored respectively in the fluctuation pattern specifying unit 157 and the biometric information prediction unit 158 to calculate the predicted value of the future user biometric information, and transmitting required information to the handheld device 110 on the basis of the predicted value. The user-specific information determination unit 160 stores a program for determining whether or not the user-specific information in the handheld device 110 matches the user-specific information stored in the user-specific information storage unit 150 of the server device 140, and when the information does not match, assuming that the user-specific information has been updated, executing the programs stored respectively in the fluctuation pattern specifying unit 157 and the biometric information prediction unit 158 to calculate the predicted value of the future user biometric information, and transmitting required information to the handheld device 110 on the basis of the predicted value and the update information of the user-specific information. The access point information determination unit 155 stores a program for determining whether or not the access point information indicating the access point to which the handheld device 110 belongs matches the access point information stored in the access point information storage unit 152 of the server device 140, and when the information does not match, assuming that the handheld device has moved to a new access point, executing the programs stored respectively in the fluctuation pattern specifying unit 157 and the biometric information prediction unit 158 to calculate the predicted value of the future user biometric information, and transmitting required information to the handheld device 110 on the basis of the predicted value and information relating to the new access point.

A flow enabling the server device 140 to provide the handheld device 110 with information using the information provision system described above with reference to FIGS. 1A and 1B will now be described using FIGS. 3 to 10. First, FIGS. 3 to 10 will be described briefly.

The flowchart in FIG. 3 illustrates biometric information profile generation processing for generating the user-specific biometric information profile as preparation for calculating the predicted value of the future user biometric information on the server device side.

Figure 4A:
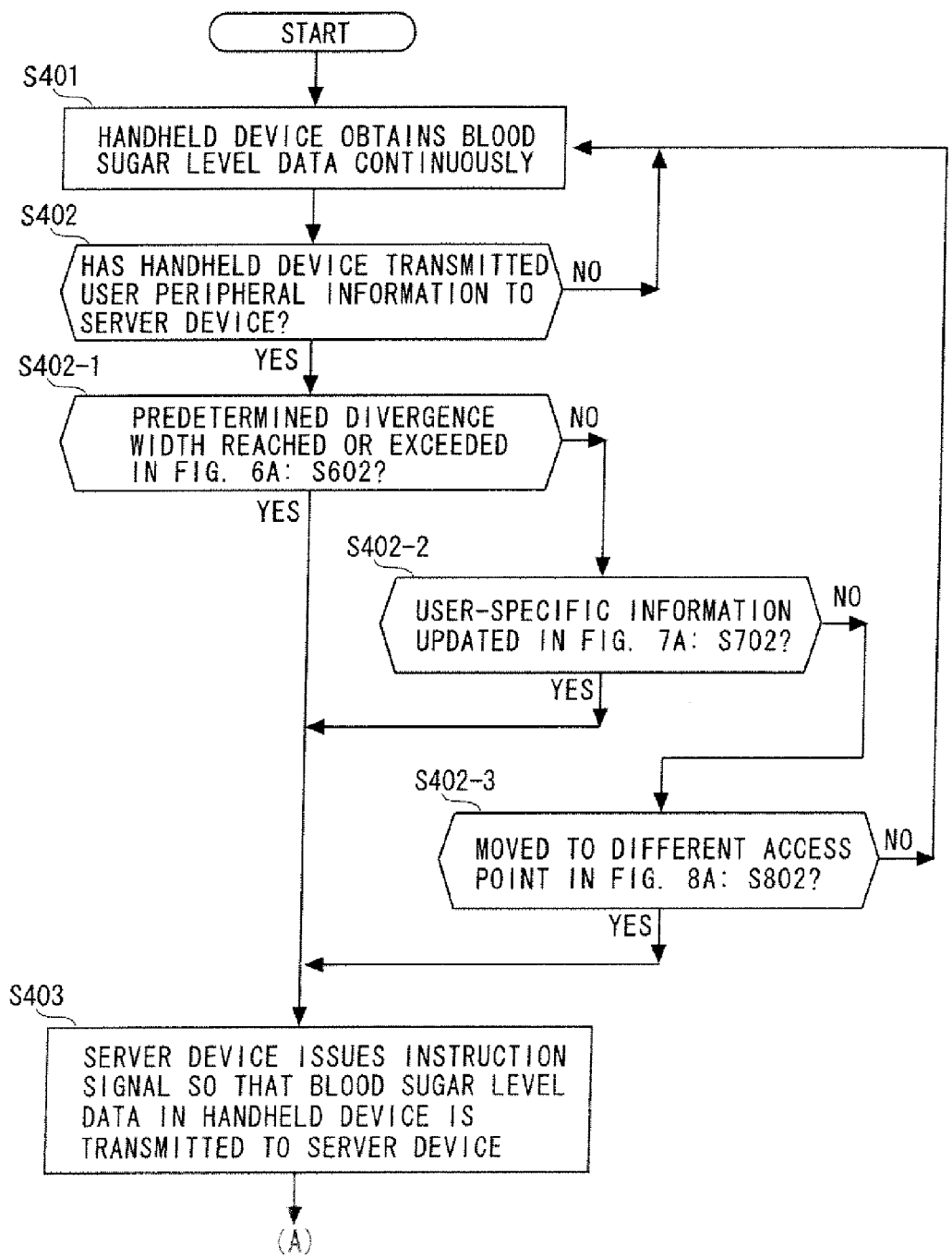
FIG. 4A is a flowchart showing processing in which the handheld device continues to obtain continuous user biometric information when no fluctuation has occurred in user peripheral information, while on the server device side, a determination is made as to whether or not a fluctuation has occurred in the user peripheral information, and when a fluctuation is acknowledged to have occurred in the user peripheral information, a predicted value of future user biometric information is calculated using the user-specific biometric information profile of FIG. 3, and after the server device completes processing for providing required information to the handheld device, the handheld device resumes continuous acquisition of the user biometric information.
Figure 4B:
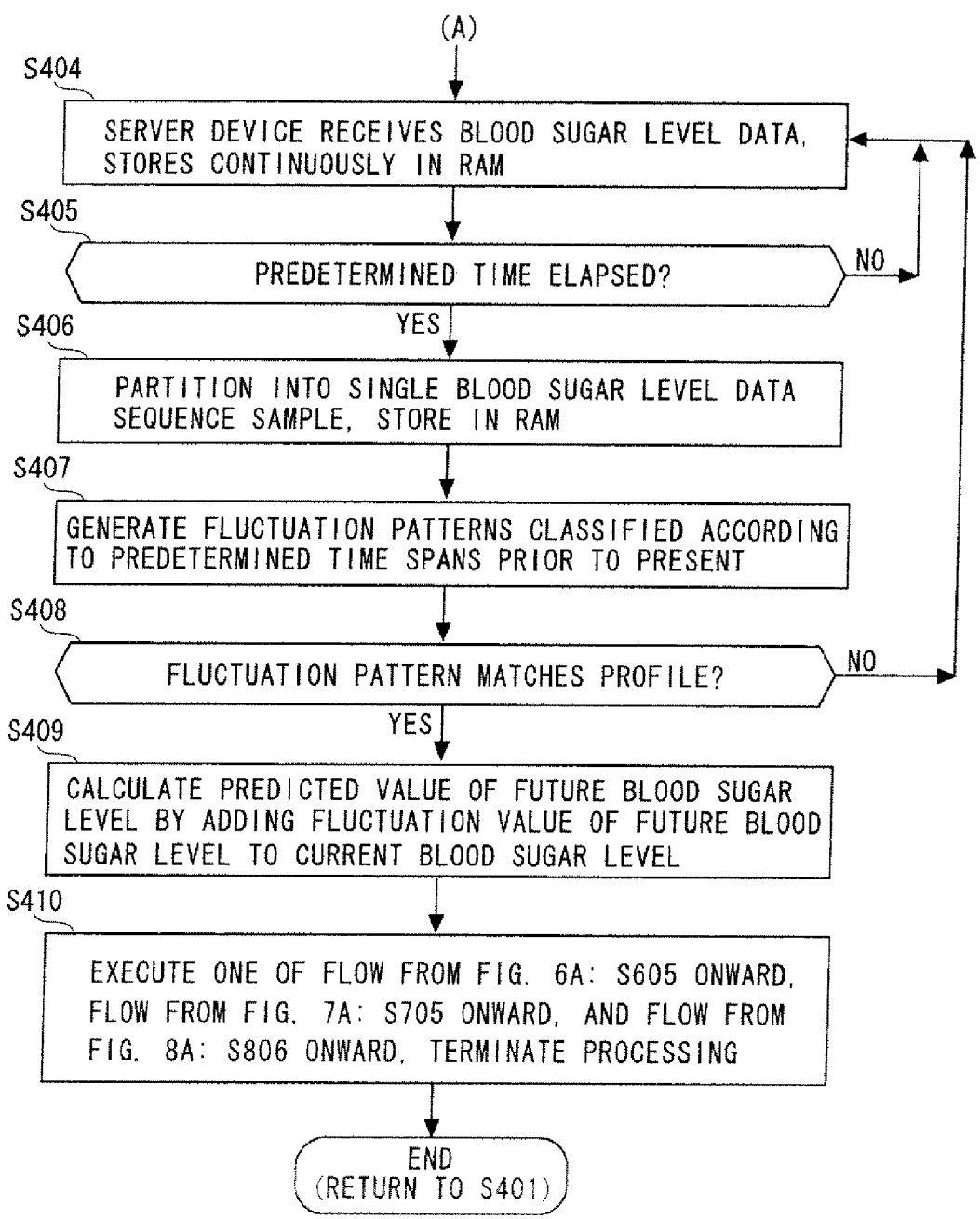
FIG. 4B is a flowchart showing processing in which the handheld device continues to obtain the continuous user biometric information when no fluctuation has occurred in the user peripheral information, while on the server device side, a determination is made as to whether or not a fluctuation has occurred in the user peripheral information, and when a fluctuation is acknowledged to have occurred in the user peripheral information, the predicted value of the future user biometric information is calculated using the user-specific biometric information profile of FIG. 3, and after the server device completes processing for providing the required information to the handheld device, the handheld device resumes continuous acquisition of the user biometric information.

In the flowcharts of FIGS. 4A and 4B, the handheld device continues to obtain the continuous user biometric information when no fluctuation has occurred in the user peripheral information, while in the flowcharts of FIGS. 6A, 7A, 8A and 9A, to be described below, a determination is made on the server device side as to whether or not a fluctuation has occurred in the user peripheral information. When a fluctuation is acknowledged to have occurred in the user peripheral information, the server device 140 calculates the predicted value of the future user biometric information using the user-specific biometric information profile. After the server device 140 completes processing for providing required information to the handheld device in the flowcharts of FIGS. 6B, 7B, 7C, 8B and 9B, to be described below, the handheld device returns to processing for continuously obtaining the user biometric information. This flow will now be described.

The flowcharts of FIGS. 6A to 9B illustrate processing in which the user biometric information, the user-specific information, and the access point information indicating the access point to which the handheld device of the user belongs are respectively used as the user peripheral information according to this embodiment, the server device 140 determines whether or not a fluctuation has occurred in this information, and when a fluctuation is acknowledged, required information is selected from this information and the predicted value of the future user biometric information and provided to the handheld device of the user. Note that in FIGS. 6A to 9B, the aforesaid three types of information are cited as the user peripheral information, but the user peripheral information is not limited thereto.

Next, the flowchart of FIG. 3 will be described in detail.

The measuring unit 112 of the handheld device 110 measures the blood sugar level of the user and obtains blood sugar level data continuously as the continuous user biometric information (step S301). As regards an operation for obtaining the blood sugar level data, the handheld device 110 may obtain the data periodically using the clock 120.

Next, the transmission/reception unit 115 of the handheld device 110 transmits the blood sugar level data of the user, obtained continuously by the measuring unit 112, to the server device 140 continuously (step S302). As regards a transmission operation and a transmission timing, the user may instruct the CPU 111 to transmit the data as desired using the input unit, or the CPU 111 may transmit the data to the server device 140 periodically using the clock 120. Note, however, that regardless of the employed method, the continuously transmitted blood sugar level data are preferably suppressed to a required minimum in order to avoid wasteful charges such as communication charges on the user. As a favorable transmission timing, the data are preferably transmitted continuously before and after daily events during which the blood sugar level of the user is likely to vary, for example eating, sleep, bathing, exercise, and administration of insulin or other medicine.

Next, when the continuously obtained blood sugar level data of the user transmitted from the handheld device 110 starts to be received in the transmission/reception unit 145 of the server device 140, the CPU 141 reads the program stored in the biometric information profile generation unit 156 of the ROM 147 to the RAM 142 to execute processing for continuously storing the continuously received blood sugar level data of the user in the RAM 142 (step S303).

Next, the CPU 141 determines whether or not a predetermined time has elapsed from the start, in the step S303, of continuous storage of the blood sugar level data of the user in the RAM 142 (step S304).

When the CPU 141 determines that the predetermined time has not elapsed in the step S304, the processing returns to the step S303. When the CPU 141 determines that the predetermined time has elapsed, on the other hand, the blood sugar level data of the user stored continuously in the RAM 142 is partitioned into a single blood sugar level data sequence sample and stored in the RAM 142 again (step S305).

Next, the CPU 141 determines whether or not the number of blood sugar level data sequence samples stored in the RAM 142 has reached a predetermined number. When the CPU 141 determines that the predetermined number of samples is not stored, the processing returns to the step S303, in which a new blood sugar level data sequence sample is stored in the RAM 142 through the processing up to the step S305. When the CPU 141 determines that the predetermined number of blood sugar level data sequence samples is stored, on the other hand, the processing advances to a step S307 (step S306).

Next, in the step S307, the CPU 141 first performs processing for calculating a divergence rate of the blood sugar level, a rate of change in the blood sugar level, and a difference in the blood sugar level exhibited by blood sugar level data sequences obtained at or before a past time P relative to each of the predetermined number of stored blood sugar level data sequence samples (expressing past user biometric information). Note that the past time P is a past time from a newest time included in each blood sugar level data sequence sample. Specific methods of calculating the divergence rate of the blood sugar level, the rate of change in the blood sugar level, and the difference in the blood sugar level will be described below.

The divergence rate of the blood sugar level is calculated using the following Equation 1, in which the blood sugar level at the past time P is DATAp and an average value of blood sugar levels measured within a time period of a predetermined length prior to A hours before the past time P is DATAf.

$$(DATAp-DATAf)/DATAf \times 100 \quad \text{(Equation 1)}$$

The rate of change in the blood sugar level is calculated using a following Equation 2, in which an average value of blood sugar levels measured within a time period of a predetermined length prior to the past time P is DATAk and the average value of the blood sugar levels measured within the time period of a predetermined length prior to A hours before the past time P is DATAf.

$$(DATAf-DATAk)/A \quad \text{(Equation 2)}$$

The difference in the blood sugar level is calculated using a following Equation 3, in which the blood sugar level at the past time P is DATAp and the blood sugar level at A hours before the past time P is DATAa.

$$DATAp-DATAa \quad \text{(Equation 3)}$$

Next, the CPU 141 calculates the divergence rate of the blood sugar level (Equation 1), the rate of change in the blood sugar level (Equation 2), and the past blood sugar level constituted by the difference in the blood sugar level (Equation 3) for each of the predetermined number of stored blood sugar level data sequence samples. The CPU 141 then performs processing to determine a pattern, from among Pattern 1 to Pattern 6 shown in FIG. 5, to which each blood sugar level data sequence sample corresponds (step S307). The CPU 141 then advances the processing to a step S308.

Next, in the step S308, the CPU 141 determines a frequency distribution of fluctuation values of the blood sugar levels measured within X hours after the past time P exhibited by the respective blood sugar level data sequence samples in relation to Pattern 1 to Pattern 6 (representing fluctuation patterns of the past user biometric information) to which the respective blood sugar level data sequence samples correspond, and calculates a median thereof as a future blood sugar level fluctuation value (i.e. a fluctuation value of the future user biometric information) from the past time P. Note that an average value of the fluctuation values of the blood sugar levels measured within X hours after the past time P may be calculated as the fluctuation value of the future user biometric information instead of the median. The CPU 141 then creates user-specific biometric information profiles associating the respective fluctuation patterns of the past user biometric information obtained in the manner described above with the future blood sugar level fluctuation values (i.e. the fluctuation values of the future user biometric information) from the time P of the corresponding fluctuation pattern. The CPU 141 stores the user-specific biometric information profiles in the profile generation storage unit 153 of the auxiliary storage unit 148 in the form of the database shown in FIG. 2D. The CPU 141 then deletes the program read from the biometric information profile generation unit 156 stored in the RAM 142 and terminates the processing. (Step S308)

Through this series of processes, the user-specific biometric information profile can be created as preparation for calculating the predicted value of the future user biometric information on the server device side.

Next, the flowcharts in FIGS. 4A and 4B will be described in detail.

When no fluctuation occurs in the user peripheral information, the measuring unit 112 of the handheld device 110 obtains the continuous user biometric information. Here, the measuring unit 112 of the handheld device 110 obtains the continuously measured blood sugar level of the user as the continuous user biometric information. In this case, the measuring unit 112 of the handheld device 110 may obtain the continuous user biometric information periodically using the clock 120. (Step S401)

Figure 6B:
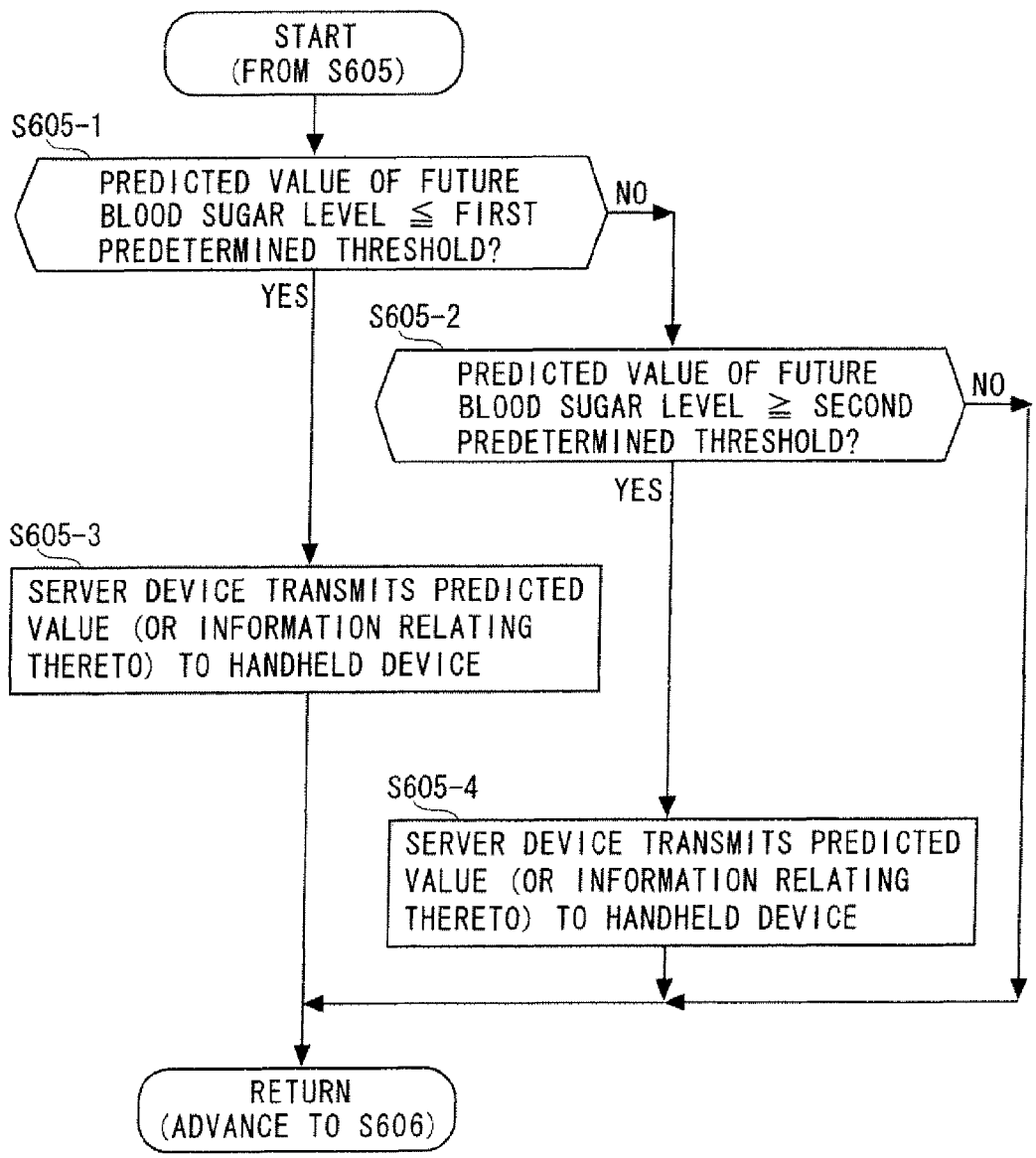
FIG. 6B is a flowchart showing processing in which the user biometric information is used as the user peripheral information, the server device determines whether or not a fluctuation has occurred therein, and when a fluctuation is acknowledged, required information is selected from this information and the predicted value of the future user biometric information and provided to the handheld device of the user.
Figure 7A:
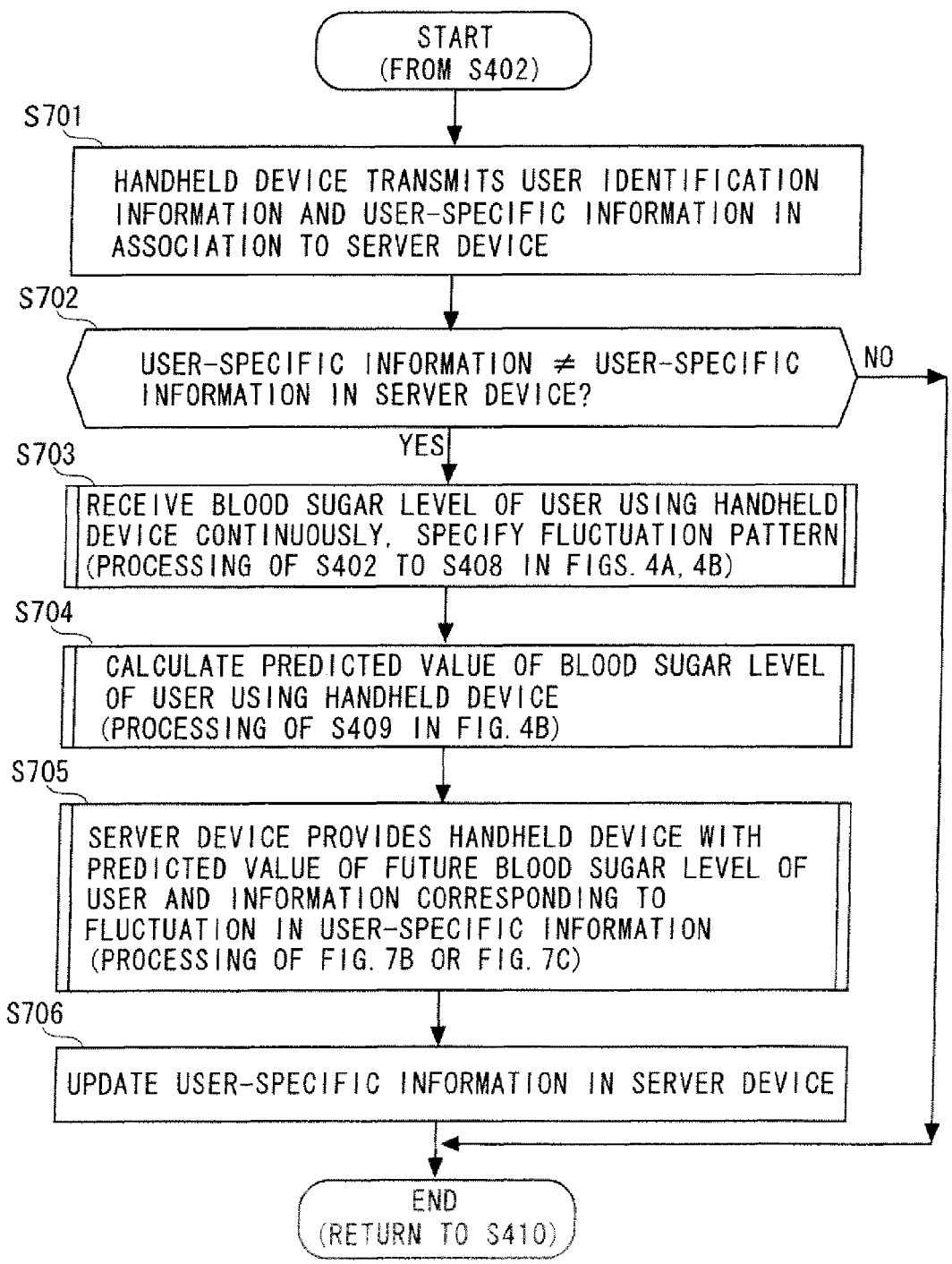
FIG. 7A is a flowchart showing processing in which the user-specific information is used as the user peripheral information, the server device determines whether or not a fluctuation has occurred therein, and when a fluctuation is acknowledged, required information is selected from this information and the predicted value of the future user biometric information and provided to the handheld device of the user.
Figure 8A:
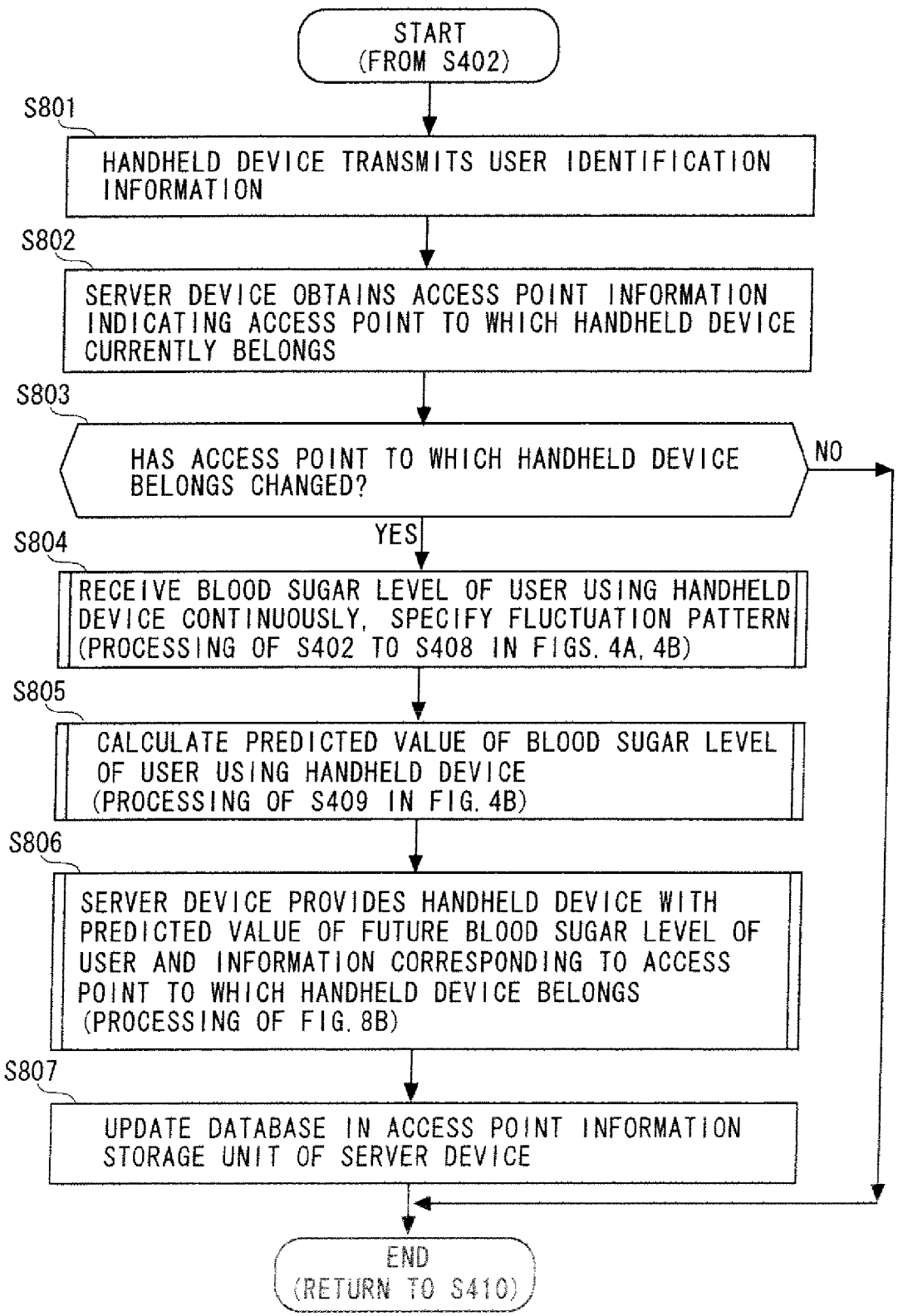
FIG. 8A is a flowchart showing processing in which access point information indicating an access point to which the handheld device of the user belongs is used as the user peripheral information, the server device determines whether or not a fluctuation has occurred therein, and when a fluctuation is acknowledged, required information is selected from this information and the predicted value of the future user biometric information and provided to the handheld device of the user.

Next, when the handheld device 110 performs processing to transmit the user peripheral information to the server device 140, the server device 140 starts the processing of one of the flowcharts shown in FIGS. 6A, 7A and 8A. This processing will be described in detail below using the flowcharts shown in FIGS. 6A, 7A and 8A. Note that when the handheld device 110 does not perform processing to transmit the user peripheral information to the server device 140, the processing returns to the step S401, where the measuring unit 112 of the handheld device 110 continues to obtain the continuous user biometric information. (Step S402)

Next, when any one of following conditions (A), (B), (C) is satisfied during the processing shown in the flowcharts of FIGS. 6A, 7A and 8A, performed by the server device 140, the server device 140 determines that a fluctuation has occurred in the user peripheral information and advances the processing to a step S403. In other cases, the processing returns to the step S401, where the measuring unit 112 of the handheld device 110 resumes continuous acquisition of the blood sugar level data.

(A) Condition (A) is satisfied when, in a step S602, to be described below, of the flowchart shown in FIG. 6A, the user biometric information transmitted from the handheld device 110 exhibits at least a predetermined divergence width relative to the user biometric information stored in the database (FIG. 2E) in the user biometric information storage unit 151 of the server device 140, or in other words when a rapid fluctuation is acknowledged to have occurred in the blood sugar level. When this fluctuation is not acknowledged, or when the processing of the flowchart in FIG. 6A is not performed, the processing advances to a step S402-2. (Step S402-1)

(B) Condition (B) is satisfied when, in a step S702, to be described below, of the flowchart shown in FIG. 7A, the user-specific information of the database (FIG. 2C) in the user-specific information storage unit 150 of the server device 140 differs from the user-specific information in the data record (FIG. 2A) transmitted from the handheld device 110, or in other words when the user-specific information (for example, everyday events during which the blood sugar level of the user is likely to vary (eating, exercise, sleep, bathing, medicine administration, and so on)) is updated in the data record (FIG. 2A). When this fluctuation is not acknowledged, or when the processing of the flowchart in FIG. 7A is not performed, the processing advances to a step S402-3. (Step S402-2)

(C) Condition (C) is satisfied when, in a step S803, to be described below, of the flowchart shown in FIG. 8A, the server device 140 determines that the handheld device 110 has moved from the access point to which it belonged to another access point. When this fluctuation is not acknowledged, the processing returns to the step S401, where the measuring unit 112 of the handheld device 110 continues to obtain the continuous user biometric information. (Step S402-3)

When anyone of the conditions of (A), (B), (C) is satisfied, the CPU 141 of the server device 140 reads the program stored in the fluctuation pattern specifying unit 157 of the ROM 147 to the RAM 142. The CPU 141 of the server device 140 then transmits an instruction signal instructing that the blood sugar level data obtained continuously by the handheld device 110 in the step S401 be transmitted continuously to the CPU 141 of the server device 140 to the CPU 111 of the handheld device 110 via the transmission/reception unit 145. (Step S403)

Next, the blood sugar level data of the user, transmitted from the handheld device 110 on the basis of the instruction signal, is received continuously in the transmission/reception unit 145 of the server device 140. The CPU 141 of the server device 140 then executes processing to store the blood sugar level data of the user continuously in the RAM 142. (Step S404)

Next, the CPU 141 determines whether or not a predetermined time has elapsed from the start of continuous storage of the blood sugar level data of the user in the RAM 142 in the step S404. When the CPU 141 determines that the predetermined time has not elapsed, the processing returns to the step S404. (Step S405)

Having determined that the predetermined time has elapsed, on the other hand, the CPU 141 partitions the blood sugar level data of the user stored continuously in the RAM 142 into a single blood sugar level data sequence and stores the partitioned sequence in the RAM 142 again. (Step S406)

Next, the CPU 141 creates a recent blood sugar level fluctuation pattern (a fluctuation pattern in recent continuous user biometric information) on the basis of the blood sugar level data sequence stored in the step S406. More specifically, the CPU 141 creates a recent blood sugar level fluctuation pattern (a fluctuation pattern in the recent continuous user biometric information) constituted by the divergence rate of the blood sugar level, the rate of change in the blood sugar level, and the difference in the blood sugar level exhibited by recent blood sugar level data sequences using a similar calculation method to that of the step S307. (Step S407)

Next, the CPU 141 determines whether or not the past user biometric information fluctuation pattern matches the recent user biometric information fluctuation pattern by referring to the user-specific biometric information profile database (FIG. 2D) stored in the profile generation storage unit 153. When a match is not determined, the CPU 141 deletes the blood sugar level data sequence stored in the RAM 142 and returns the processing to the step S404. (Step S408)

When a match is determined in the step S408, the CPU 141 deletes the program read from the fluctuation pattern specifying unit 157 and stored in the RAM 142, and reads the program stored in the biometric information prediction unit 158 of the ROM 147 to the RAM 142. The CPU 141 then refers to the user-specific biometric information profile database (FIG. 2D) to perform processing for calculating the predicted value of the future blood sugar level (a predicted value of the future user biometric information) by adding the fluctuation value of the future blood sugar level from the time P (the fluctuation value of the future user biometric information), which is associated with the matching past user biometric information fluctuation pattern, to the current blood sugar level. The CPU 141 then stores the calculated predicted value of the future blood sugar level in the RAM 142. The CPU 141 then deletes the program read from the biometric information prediction unit 158 and stored in the RAM 142, and terminates the processing for calculating the predicted value of the future blood sugar level. Following termination, the processing advances to a step S410, (Step S409)

Next, in the step S410, the CPU 141 continues to execute the processing of one of the flowcharts in FIGS. 6A, 7A and 8A, which was started in the step S402. In other words, the CPU 141 executes the processing of a step S605 onward in the flowchart of FIG. 6A, a step S705 onward in the flowchart of FIG. 7A, and a step S806 onward in the flowchart of FIG. 8A. This processing will be described in detail below with reference to the flowcharts of FIGS. 6A, 7A and 8A. When this processing is complete, the processing returns to the step S401, where the measuring unit 112 of the handheld device 110 continues to obtain the continuous user biometric information. (Step S410)

Through this series of processes, the continuous user biometric information is obtained continuously by the handheld device 110 when no fluctuation has occurred in the user peripheral information. On the server device 140 side, meanwhile, a determination is made as to whether or not a fluctuation has occurred in the user peripheral information. When a fluctuation is determined to have occurred in the user peripheral information, the server device 140 calculates the predicted value of the future user biometric information using the user-specific biometric information profile. When the processing for causing the server device 140 to provide the handheld device 110 with required information is complete, the processing for continuously obtaining the user biometric information can be resumed in the handheld device 110.

Further, the biometric information profile generation unit 156, fluctuation pattern specifying unit 157, and biometric information prediction unit 158 are used to calculate the predicted value of the future user biometric information using the calculation method described above, but the calculation method is not limited to that described above, and instead, for example, a method described in Japanese Patent Application Publication No. 2005-308742 may be used as the method of predicting the future blood sugar level.

Note that the biometric information profile generation unit 156, fluctuation pattern specifying unit 157, and biometric information prediction unit 158 may be provided in the ROM 117 of the handheld device 110 rather than the ROM 147 of the server device 140. Further, the auxiliary storage unit 116 of the handheld device 110 may include the profile generation storage unit 153. In this case, the CPU 111 of the handheld device 110 may read the various programs stored in the ROM 117 to the RAM 118 and perform virtually identical processing to the processing performed by the CPU 141 of the server device 140, described using FIGS. 3, 4A, 4B and 5. Note that in this case, when one of the conditions (A), (B), (C) is determined by the server device 140 to be satisfied (step S402-1, step S402-2, step S402-3), the CPU 141 of the server device 140 transmits an instruction signal instructing execution of the following processing to the CPU 111 of the handheld device 110 in the following step S403. Specifically, the CPU 111 of the handheld device 110 reads the program stored in the fluctuation pattern specification unit in the ROM 117 of the handheld device 110 to the RAM 118 of the handheld device 110. The CPU 111 of the handheld device 110 then executes the processing of the program (steps S403 to S409), and then executes processing to transmit the calculated predicted value of the future blood sugar level to the CPU 141 of the server device. By storing the various programs stored in the biometric information profile generation unit 156, fluctuation pattern specifying unit 157, and biometric information prediction unit 158 in the ROM 117 of the handheld device 110 and having the CPU 111 of the handheld device 110 execute the processing in this manner, a processing load on the server device can be lightened.

Next, the flowcharts shown in FIGS. 6A and 63 will be described in detail.

The CPU 111 of the handheld device 110 transmits the user biometric information stored in the measurement data storage unit 126 to the server device 140 in association with the user identification information of the handheld device 110. As regards the transmission operation and transmission timing, the user may instruct the CPU 111 to transmit the information as desired using the input unit, or the CPU 111 may transmit the information to the server device 140 automatically at the same time as new user biometric information is input into the measurement data storage unit 126. Alternatively, the CPU 111 may transmit the newest user biometric information input into the measurement data storage unit 126 to the server device 140 periodically using the clock 120. Note, however, that regardless of the employed method, the user biometric information, from the continuous user biometric information stored in the measurement data storage unit 126, is used in order to avoid excessive charges such as communication charges on the user. (Step S601)

Next, the CPU 141 of the server device 140 receives the user biometric information transmitted from the handheld device 110, stores the received information in the RAM 142, reads the program stored in the user biometric information determination unit 159 of the ROM 147 to the RAM 142, and executes the following processing. First, the CPU 141 of the server device 140 refers to the user biometric information storage unit 151 of the server device 140. Next, the CPU 141 of the server device 140 compares the user biometric information stored in the database (FIG. 2E) of the user biometric information storage unit 151 in the server device 140 with the user biometric information transmitted from the handheld device 110. In this case, the user biometric information stored in the database (FIG. 2E) of the user biometric information storage unit 151 in the server device 140 is specified on the basis of the user identification information transmitted from the handheld device 110. When the user biometric information transmitted from the handheld device 110 exhibits at least a predetermined divergence width from the user biometric information stored in the database (FIG. 2E) of the user biometric information storage unit 151 in the server device, the processing advances to a step S603. In this case, it may be acknowledged that a rapid fluctuation has occurred in the blood sugar level, for example. Further, the server device 140 determines that a fluctuation has occurred in the user peripheral information. When the divergence width is smaller than the predetermined width, the processing advances to a step S606. In this case, the server device determines that a fluctuation has not occurred in the user peripheral information. (Step S602)

Next, in steps S603 and S604, the CPU 141 of the server device 140 reads and executes the programs stored respectively in the fluctuation pattern specifying unit 157 and the biometric information prediction unit 158 of the server device 140 in accordance with the flow of the steps S402 to S409. The CPU 141 of the server device 140 thus calculates the final predicted value of the future blood sugar level and stores the predicted value of the future blood sugar level in the RAM 142. (Steps S603, S604)

Next, the server device 140 provides the handheld device 110 with information corresponding to the predicted value of the future blood sugar level calculated in the step S604. This provision processing is performed through steps S605-1 to S605-4 shown in FIG. 6B. (Step S605)

In the step S605-1, the CPU 141 of the server device 140 determines whether or not the predicted value of the future blood sugar level is equal to or smaller than a first predetermined threshold. When the predicted value of the future blood sugar level is equal to or smaller than the first predetermined threshold, the processing advances to the step S605-3. When the predicted value of the future blood sugar level is larger than the first predetermined threshold, the processing advances to the step S605-2. (Step S605-1)

In the step S605-3, the server device 140 transmits the predicted value of the future blood sugar level or information relating to the predicted value of the future blood sugar level to the handheld device 110 via the transmission/reception unit 145. The information relating to the predicted value of the future blood sugar level is information indicating the possibility of lapsing into a low blood sugar condition in the near future, corresponding warning information, information describing countermeasures for avoiding lapsing into a low blood sugar condition in the future, and so on. The server device 140 may transmit the predicted value of the future blood sugar level and the information relating to the predicted value of the future blood sugar level simultaneously. The predicted value of the future blood sugar level and the information relating to the predicted value of the future blood sugar level are received via the transmission/reception unit 115 of the handheld device 110 and displayed on the display unit 122 of the handheld device 110. (Step S605-3)

In the step S605-2, the CPU 141 of the server device 140 determines whether or not the predicted value of the future blood sugar level is equal to or larger than a second predetermined threshold. When the predicted value of the future blood sugar level is equal to or larger than the second predetermined threshold, the processing advances to the step S605-4. When the predicted value of the future blood sugar level is smaller than the second predetermined threshold, this indicates that there is no information to be transmitted to the handheld device 110 from the server device 140, and therefore the series of processes shown in FIG. 6B is terminated, whereupon the processing advances to a step S606. (Step S605-2)

In the step S605-4, the server device 140 transmits the predicted value of the future blood sugar level or information relating to the predicted value of the future blood sugar level to the handheld device 110 via the transmission/reception unit 145. The information relating to the predicted value of the future blood sugar level is information indicating the possibility of lapsing into a high blood sugar condition in the near future, corresponding warning information, information describing countermeasures for avoiding lapsing into a high blood sugar condition in the future, and so on. The server device 140 may transmit the predicted value of the future blood sugar level and the information relating to the predicted value of the future blood sugar level simultaneously. The predicted value of the future blood sugar level and the information relating to the predicted value of the future blood sugar level are received via the transmission/reception unit 115 of the handheld device 110 and displayed on the display unit 122 of the handheld device 110. (Step S605-4)

In the steps S605-1 to S605-4, a series of processes is performed for providing the handheld device 110 with information corresponding to the calculated predicted value of the future blood sugar level. When this processing is complete, the processing advances to the step S606.

Finally, in the step S606, the CPU 141 of the server device 140 updates the user biometric information in the database (FIG. 2E) of the user biometric information storage unit 151 in the server device 140 to the user biometric information transmitted from the handheld device 110. Following the update, the CPU 141 of the server device 140 deletes the user biometric information read to the RAM 142 and the program read from the user biometric information determination unit 159, and then terminates the processing. (Step S606)

Through the series of processes shown in FIGS. 6A and 6B, the server device 140 can receive only required information on the basis of the user biometric information transmitted from the handheld device 110, determine whether or not the user is in a case of lapsing into a low blood sugar condition or a high blood sugar condition in the future, and transmit a predicted value of the future blood sugar level and information relating thereto to the handheld device 110 while suppressing wasteful charges such as communication charges as far as possible. Through this series of processes, the user is able to implement countermeasures on the basis of the transmitted information.

Note that the predetermined divergence width (step S602), the first predetermined threshold (step S605-1), and the second predetermined threshold (step S605-2) shown in FIGS. 6A and 6B may be set as desired on the user side or set in advance on the server device side, and are not limited to the above description. Further, the series of processes for providing the handheld device 110 with the information corresponding to the calculated predicted value of the future blood sugar level in the steps S605-1 to S605-4 is not limited to this flow. For example, one, three, or more thresholds may be prepared instead of the first and second predetermined thresholds, and in addition to the predicted value of the future blood sugar level, information corresponding to respective ranges of the predicted value may be transmitted to the handheld device 110.

Next, the flowcharts shown in FIGS. 7A, 7B and 7C will be described in detail.

The CPU 111 of the handheld device 110 transmits the data record (which is associated with the user identification information of the handheld device 110; shown in FIG. 2A) stored in the user-specific information storage unit 125 to the server device 140. As regards the transmission operation, the user may instruct the CPU 111 to transmit the data record as desired using the input unit, or the CPU 111 may transmit the data record periodically. Alternatively, the user may input the newest user-specific information into the handheld device 110, and at the same time as the CPU 111 updates the data record stored in the user-specific information storage unit 125, the data record may be transmitted to the server device 140 automatically. (Step S701)

Next, the CPU 141 of the server device 140 receives the data record (FIG. 2A) transmitted from the handheld device 110, stores the received data record in the RAM 142, reads the program stored in the user-specific information determination unit 160 of the ROM 147 to the RAM 142, and executes the following processing. First, the CPU 141 of the server device 140 refers to the user-specific information storage unit 150 of the server device 140. Next, the CPU 141 of the server device 140 compares the user-specific information stored in the database (FIG. 2C) of the user-specific information storage unit 150 in the server device 140 with the user-specific information in the data record (FIG. 2A) transmitted from the handheld device 110. In this case, the user-specific information stored in the database (FIG. 2C) of the user-specific information storage unit 150 in the server device 140 is specified on the basis of the user identification information transmitted from the handheld device 110. When the information is different, or in other words when the information relating to the everyday events during which the blood sugar level of the user is likely to vary (eating, sleep, bathing, exercise, medicine administration, and so on) has been updated as shown in FIG. 2A, the processing advances to a step S703. In this case, carbohydrates may have been newly ingested during a meal or medicine may have been administered, for example. Further, the server device 140 determines that a fluctuation has occurred in the user peripheral information. When the information matches, the CPU 141 deletes the data record (FIG. 2A) stored in the RAM 142 and the program read from the user-specific information determination unit 160, and terminates the processing. In this case, the server device 140 determines that no fluctuation has occurred in the user peripheral information. (Step S702)

Next, in steps S703 and S704, the CPU 141 of the server device 140 reads and executes the programs stored respectively in the fluctuation pattern specifying unit 157 and the biometric information prediction unit 158 in accordance with the flow of the steps S402 to S409. The CPU 141 of the server device 140 thus calculates the final predicted value of the future blood sugar level and stores the predicted value of the future blood sugar level in the RAM 142. (Steps S703, S704)

Next, the server device 140 provides the handheld device 110 with the predicted value of the future blood sugar level calculated in the step S704, and information corresponding to the updated user-specific information (for example, everyday events during which the blood sugar level of the user is likely to vary (eating, exercise, sleep, bathing, medicine administration, and so on)). A case in which the medicine dosage of the user-specific information is updated (steps S705-1 to S705-4) will be described as examples using FIG. 7B. Further, a case in which the eating information of the user-specific information (a carbohydrate intake during a meal) is updated (steps S705-A to S705-D) will be described as examples using FIG. 7C. (Step S705)

First, the example shown in FIG. 7B will be described. When the medicine dosage (an amount of a blood sugar level lowering agent such as insulin administered to the user, for example) has been updated in the step S705-1, the CPU 141 of the server device 140 determines whether or not the medicine dosage is larger than a predetermined dosage. When the medicine dosage is larger than the predetermined dosage, the processing advances to the step S705-2. When the medicine dosage is equal to or smaller than the predetermined dosage, this indicates that there is no information to be provided to the handheld device 110 from the server device 140, and therefore the series of processes shown in FIG. 7B is terminated, whereupon the processing advances to the step S706. (Step S705-1)

In the step S705-2, the CPU 141 of the server device 140 determines whether or not the calculated predicted value of the future blood sugar level is equal to or smaller than a first predetermined threshold. When the predicted value of the future blood sugar level is equal to or smaller than the first predetermined threshold, the processing advances to the step S705-3. When the predicted value of the future blood sugar level is larger than the first predetermined threshold, the processing advances to the step S705-4. (Step S705-2)

In the step S705-3, the server device 140 transmits the predicted value of the future blood sugar level or information relating to the predicted value of the future blood sugar level to the handheld device 110 via the transmission/reception unit 145. The information relating to the predicted value of the future blood sugar level is information indicating the possibility of lapsing into a low blood sugar condition in the near future, corresponding warning information, information describing countermeasures for avoiding lapsing into a low blood sugar condition in the future, and so on. The server device 140 may transmit the predicted value of the future blood sugar level and the information relating to the predicted value of the future blood sugar level to the handheld device 110 simultaneously. The predicted value of the future blood sugar level and the information relating to the predicted value of the future blood sugar level are received via the transmission/reception unit 115 of the handheld device 110 and displayed on the display unit 122 of the handheld device 110. (Step S705-3)

In the step S705-4, the server device 140 transmits a message indicating that the medicine dosage is excessive to the handheld device 110 via the transmission/reception unit 145. In addition to the message indicating that the medicine dosage is excessive, the server device 140 may also transmit information relating thereto. The related information is information indicating the danger of an excessive medicine dosage, countermeasures to be taken in such cases, and so on. The transmitted message and related information are received via the transmission/reception unit 115 of the handheld device 110 and displayed on the display unit 122 of the handheld device 110. (Step S705-4)

In the steps S705-1 to S705-4, a series of processes is performed to provide the handheld device 110 with the calculated predicted value of the future blood sugar level and information corresponding to the updated user-specific information (in this example, the medicine dosage is cited as an everyday event during which the blood sugar level of the user is likely to vary). Once this processing is complete, the processing advances to the step S706.

Next, the example shown in FIG. 7C will be described. When the carbohydrate intake during a meal is updated in the step S705-A, the CPU 141 of the server device 140 determines whether or not the carbohydrate intake is larger than a predetermined intake. When the carbohydrate intake is larger than the predetermined carbohydrate intake, the processing advances to the step S705-B. When the carbohydrate intake is equal to or smaller than the predetermined intake, this indicates that there is no information to be provided to the handheld device 110 from the server device 140, and therefore the series of processes shown in FIG. 7C is terminated, whereupon the processing advances to the step S706. (Step S705-A)

In the step S705-B, the CPU 141 of the server device 140 determines whether or not the calculated predicted value of the future blood sugar level is equal to or larger than a second predetermined threshold. When the predicted value of the future blood sugar level is equal to or larger than the second predetermined threshold, the processing advances to the step S705-C. When the predicted value of the future blood sugar level is smaller than the second predetermined threshold, the processing advances to the step S705-D. (Step S705-B)

In the step S705-C, the server device 140 transmits the predicted value of the future blood sugar level or information relating to the predicted value of the future blood sugar level to the handheld device 110 via the transmission/reception unit 145. The information relating to the predicted value of the future blood sugar level is information indicating the possibility of lapsing into a high blood sugar condition in the near future, corresponding warning information, information describing countermeasures for avoiding lapsing into a high blood sugar condition in the future, and so on. The server device 140 may transmit the predicted value of the future blood sugar level and the information relating to the predicted value of the future blood sugar level simultaneously. The predicted value of the future blood sugar level and the information relating to the predicted value of the future blood sugar level are received via the transmission/reception unit 115 of the handheld device 110 and displayed on the display unit 122 of the handheld device 110. (Step S705-C)

In the step S705-D, the server device 140 transmits a message indicating that the carbohydrate intake is excessive to the handheld device 110 via the transmission/reception unit 145. In addition to the message indicating that the carbohydrate intake is excessive, the server device 140 may also transmit information relating thereto. The related information is information indicating the danger of an excessive carbohydrate intake, countermeasures to be taken in such cases, and so on. The transmitted message and related information are received via the transmission/reception unit 115 of the handheld device 110 and displayed on the display unit 122 of the handheld device 110. (Step S705-D)

In the steps S705-A to S705-D, a series of processes is performed to provide the handheld device 110 with the calculated predicted value of the future blood sugar level and information corresponding to the updated user-specific information (in this example, the carbohydrate intake during a meal is cited as an everyday event during which the blood sugar level of the user is likely to vary). When this processing is complete, the processing advances to the step S706.

Finally, in the step S706, the CPU 141 of the server device 140 updates the user-specific information in the database (FIG. 2C) of the user-specific information storage unit 150 in the server device 140 to the user-specific information in the data record (FIG. 2A) transmitted from the handheld device 110. Following the update, the CPU 141 of the server device 140 deletes the data record (FIG. 2A) read to the RAM 142 and the program read from the user-specific information determination unit 160, and then terminates the processing. (Step S706)

Figure 7B:
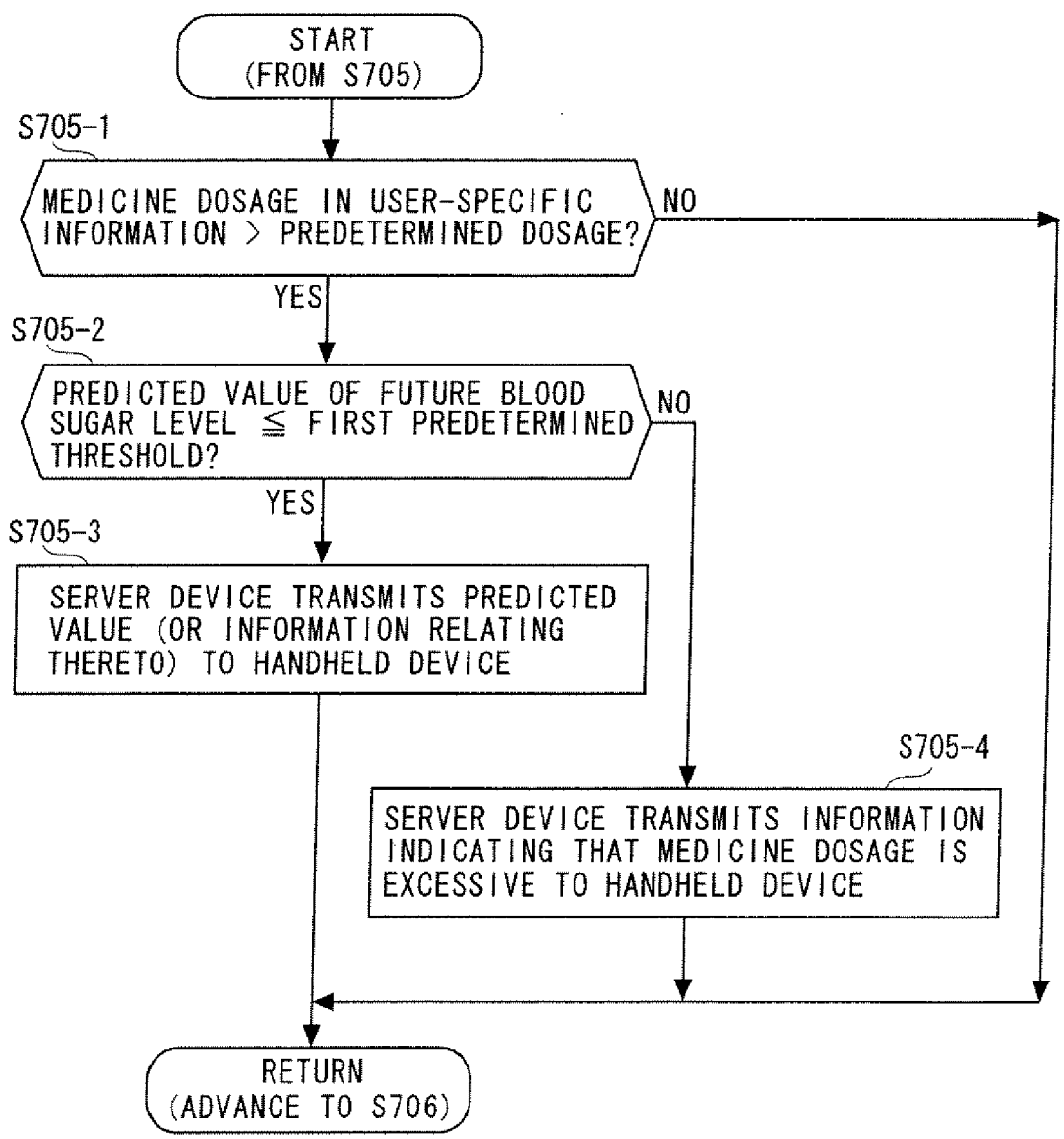
FIG. 7B is a flowchart showing processing in which the user-specific information is used as the user peripheral information, the server device determines whether or not a fluctuation has occurred therein, and when a fluctuation is acknowledged, required information is selected from this information and the predicted value of the future user biometric information and provided to the handheld device of the user.
Figure 7C:
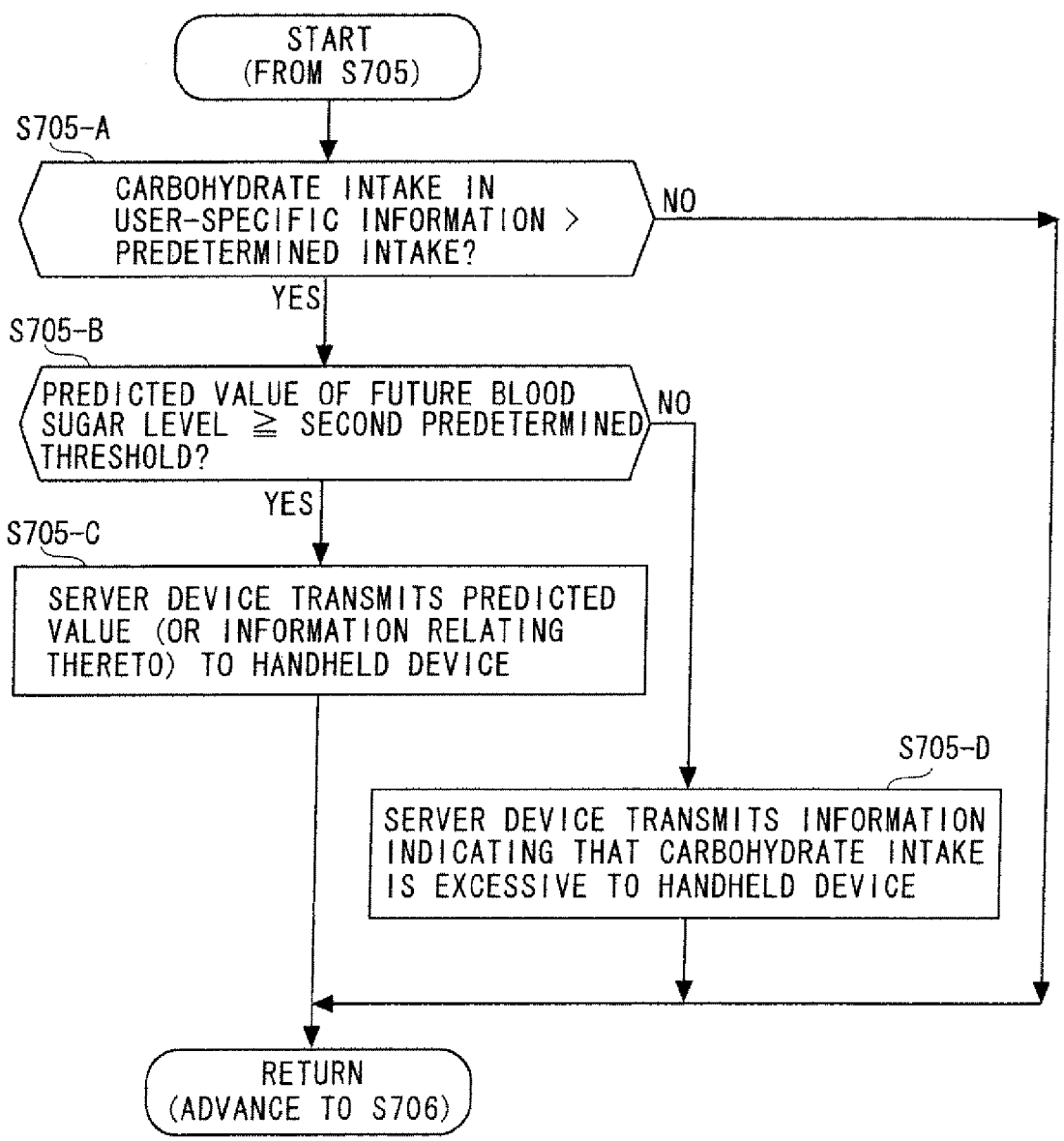
FIG. 7C is a flowchart showing processing in which the user-specific information is used as the user peripheral information, the server device determines whether or not a fluctuation has occurred therein, and when a fluctuation is acknowledged, required information is selected from this information and the predicted value of the future user biometric information and provided to the handheld device of the user.

Through the series of processes shown in FIGS. 7A to 7C, the server device 140 can receive only required information on the basis of an update of the user-specific information transmitted from the handheld device 110, determine whether or not the user is in a case of lapsing into a low blood sugar condition or a high blood sugar condition in the future, and transmit a predicted value of the future blood sugar level and information relating thereto to the handheld device 110 in accordance with the content of the update of the user-specific information while suppressing wasteful charges such as communication charges as far as possible. Through this series of processes, the user is able to implement countermeasures on the basis of the transmitted information.

Note that the first predetermined threshold (step S705-2) and the second predetermined threshold (step S705-B) shown in FIGS. 7A to 7C may be set as desired on the user side or set in advance on the server device side, and are not limited to the above description. Further, the processing of the steps S705-1 to S705-4 and the processing of the steps S705-A to S705-D are not limited to these flows. For example, one, three, or more thresholds may be prepared instead of the first and second predetermined thresholds, and in addition to the predicted value of the future blood sugar level, information corresponding to respective ranges of the predicted value may be transmitted to the handheld device 110.

Note that FIG. 7B shows an example in which the medicine dosage of the user-specific information is updated (steps S705-1 to S705-4) and FIG. 7C shows an example in which the eating information of the user-specific information (the carbohydrate intake during a meal) is updated (steps S705-A to S705-D). By performing the series of processes shown in FIG. 7B or FIG. 7C, for example, in a case where other user-specific information (for example, the bathing information, exercise information, and so on) is updated, the server device 140 can receive only required information on the basis of the update of the user-specific information transmitted from the handheld device 110, determine whether or not the user is in a case of lapsing into a low blood sugar condition or a high blood sugar condition in the future, and transmit a predicted value of the future blood sugar level and information relating thereto to the handheld device 110 in accordance with the content of the update of the user-specific information while suppressing wasteful charges such as communication charges as far as possible. Through this series of processes, the user is able to implement countermeasures on the basis of the transmitted information. Needless to say, this case is also not limited to the flows shown in FIGS. 7B and 7C.

Next, the flowcharts shown in FIGS. 8A and 8B will be described in detail.

The CPU 111 of the handheld device 110 periodically transmits the user identification information stored in the user identification information storage unit 124 in the form of a signal. The access points 130 capable of receiving the signal attach access point information allocated to each individual access point and a reception strength to the signal, and transmit the signal to the server device 140. (Step S801)

Next, the CPU 141 of the server device 140 receives the user identification information, access point information, and reception strength transmitted via the access point in the step S801, and stores the received information in the RAM 142. The CPU 141 of the server device 140 then reads the program stored in the access point information determination unit 155 of the ROM 147 to the RAM 142, and executes the following processing. First, the CPU 141 of the server device 140 compares the reception strengths transmitted from the individual access points in the step S801. The CPU 141 of the server device 140 then selects the access point information received with the greatest reception strength and stores the selected access point information in the RAM 142 in association with the user identification information. The CPU 141 of the server device 140 then deletes the other access point information and reception strength information. Through this processing, the server device 140 obtains the access point information indicating the access point to which the handheld device 110 currently belongs. (Step S802)

Next, the CPU 141 of the server device 140 refers to the database (FIG. 2B) in the access point information storage unit 152 of the auxiliary storage unit 148 to retrieve user identification information that matches the user identification information stored in the step S802, and specifies the access point information associated with the retrieved user identification information. The CPU 141 of the server device 140 then compares the specified access point information with the access point information stored in the RAM 142. When the specified access point information and the access point information stored in the RAM 142 are different, or in other words when the CPU 141 of the server device 140 determines that the handheld device 110 has moved from the access point to which it belonged to another access point, the processing advances to a step S804. In this case, the server device 140 determines that a fluctuation has occurred in the user peripheral information. When the specified access point information and the access point information stored in the RAM 142 match, the server device 140 determines that the handheld device 110 remains at the same access point. In this case, the CPU 141 of the server device 140 deletes the user identification information and access point information stored in the RAM 142 and the program read from the access point information determination unit 155, and terminates the processing. In this case, the server device 140 determines that no fluctuation has occurred in the user peripheral information. (Step S803)

Next, insteps S804 and S805, the CPU 141 of the server device 140 reads and executes the programs stored respectively in the fluctuation pattern specifying unit 157 and the biometric information prediction unit 158 in accordance with the flow of the steps S402 to S409. The CPU 141 of the server device 140 thus calculates the final predicted value of the future blood sugar level and stores the predicted value of the future blood sugar level in the RAM 142. (Steps S804, S805)

Next, the server device 140 provides the handheld device 110 with the predicted value of the future blood sugar level calculated in the step S805 and information corresponding to the access point to which the handheld device 110 currently belongs (the new access point to which the handheld device 110 is determined to have moved in the step S803). This provision processing is performed through steps S806-1 to S806-5 shown in FIG. 8B. (Step S806)

In the step S806-1, the CPU 141 of the server device 140 determines whether or not the predicted value of the future blood sugar level is equal to or smaller than a first predetermined threshold. When the predicted value of the future blood sugar level is equal to or smaller than the first predetermined threshold, the processing advances to the step S806-3. When the predicted value of the future blood sugar level is larger than the first predetermined threshold, the processing advances to the step S806-2. (Step S806-1)

In the step S806-3, the server device 140 transmits the predicted value of the future blood sugar level or information indicating medical institutions belonging to the new access point of the handheld device 110 to the handheld device 110 via the transmission/reception unit 145. The medical institution information is obtained by referring to the information stored in the access point area information storage unit 154 of the server device 140, and indicates, but is not limited to, the addresses, contact addresses, and map positions of the medical institutions. The server device 140 may also transmit information relating to the predicted value of the future blood sugar level. The related information is information indicating the possibility of lapsing into a low blood sugar condition in the near future, corresponding warning information, information describing countermeasures for avoiding lapsing into a low blood sugar condition in the future, and so on. The server device 140 may transmit the predicted value of the future blood sugar level, the medical institution information, and the information relating to the predicted value of the future blood sugar level simultaneously. Further, the server device 140 may transmit any one of the predicted value of the future blood sugar level, the medical institution information, and the information relating to the predicted value of the future blood sugar level. The information is received via the transmission/reception unit 115 of the handheld device 110 and displayed on the display unit 122 of the handheld device 110. (Step S806-3)

In the step S806-2, the CPU 141 of the server device 140 determines whether or not the predicted value of the future blood sugar level is equal to or larger than a second predetermined threshold. When the predicted value of the future blood sugar level is equal to or larger than the second predetermined threshold, the processing advances to the step S806-4. When the predicted value of the future blood sugar level is smaller than the second predetermined threshold, the processing advances to the step S806-5. (Step S806-2)

In the step S806-4, the server device 140 transmits the predicted value of the future blood sugar level or the information indicating the medical institutions belonging to the new access point of the handheld device 110 to the handheld device 110 via the transmission/reception unit 145. The medical institution information is obtained by referring to the information stored in the access point area information storage unit 154 of the server device 140, and indicates, but is not limited to, the addresses, contact addresses, and map positions of the medical institutions. The server device 140 may also transmit the information relating to the predicted value of the future blood sugar level. The related information is information indicating the possibility of lapsing into a high blood sugar condition in the near future, corresponding warning information, information describing countermeasures for avoiding lapsing into a high blood sugar condition in the future, and so on. The server device 140 may transmit the predicted value of the future blood sugar level, the medical institution information, and the information relating to the predicted value of the future blood sugar level simultaneously. Further, the server device 140 may transmit any one of the predicted value of the future blood sugar level, the medical institution information, and the information relating to the predicted value of the future blood sugar level. The information is received via the transmission/reception unit 115 of the handheld device 110 and displayed on the display unit 122 of the handheld device 110. (Step S806-4)

In the step S806-5, the server device 140 transmits area information relating to the new access point of the handheld device 110 to the handheld device 110 via the transmission/reception unit 145. The area information may be addresses, contact addresses, and map positions of drugstores and pharmacies, daily weather information or typical climate information relating to the access point, dietary habit information, and so on, for example, but as long as the information is unique to the area of the access point, the information is not limited to these examples. Note that this information is obtained by referring to the information stored in the access point area information storage unit 154 of the server device 140. The transmitted information is received via the transmission/reception unit 115 of the handheld device 110 and displayed on the display unit 122 of the handheld device 110. (Step S806-5)

In the steps S806-1 to S806-5, a series of processes is performed to provide the handheld device 110 with the calculated predicted value of the future blood sugar level and information corresponding to the access point to which the handheld device 110 currently belongs (the access point to which the handheld device 110 is determined to have moved in the step S803). When this processing is complete, the processing advances to the step S807.

Finally, in the step S807, the CPU 141 of the server device 140 updates the access point information in the database (FIG. 2B) of the access point information storage unit 152 in the server device 140 to the access point information specified and stored in the RAM 142 in the step S803. Following the update, the CPU 141 of the server device 140 deletes the access point information specified and stored in the RAM 142 in the step S803 and the program read from the access point information determination unit 155. (Step S807)

Figure 8B:
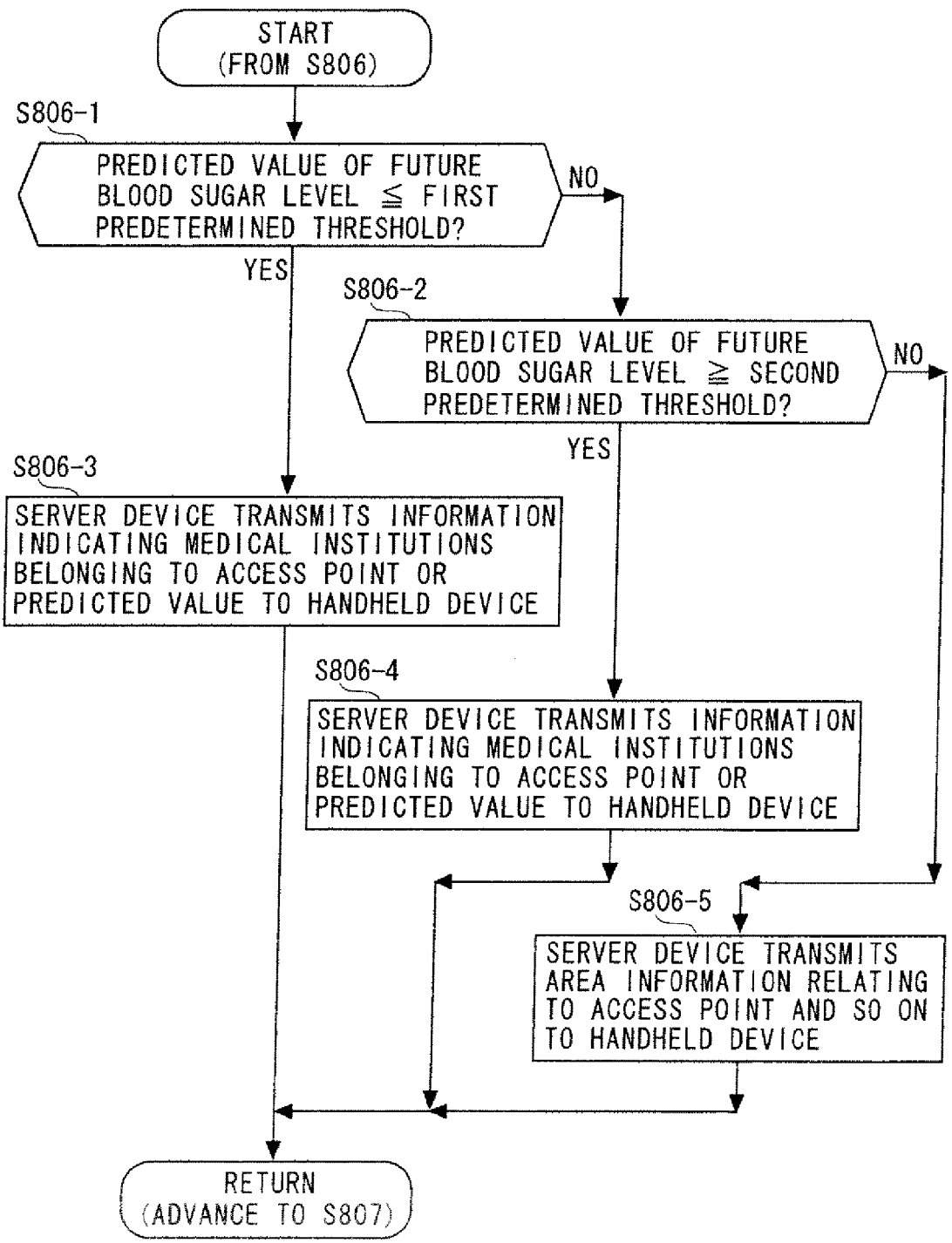
FIG. 8B is a flowchart showing processing in which the access point information indicating the access point to which the handheld device of the user belongs is used as the user peripheral information, the server device determines whether or not a fluctuation has occurred therein, and when a fluctuation is acknowledged, required information is selected from this information and the predicted value of the future user biometric information and provided to the handheld device of the user.

Through the series of processes shown in FIGS. 8A and 8B, the server device 140 can receive only required information on the basis of the access point information transmitted from the handheld device 110, determine whether or not the user is in a case of lapsing into a low blood sugar condition or a high blood sugar condition in the future, and transmit a predicted value of the future blood sugar level and information relating thereto to the handheld device 110 while suppressing wasteful charges such as communication charges as far as possible. Through this series of processes, the user is able to implement countermeasures on the basis of the transmitted information.

Note that the first predetermined threshold (step S806-1), and the second predetermined threshold (step S806-2) shown in FIG. 8B may be set as desired on the user side or set in advance on the server device side, and are not limited to the above description. Further, the series of processes for providing the handheld device 110 with the information corresponding to the calculated predicted value of the future blood sugar level in the steps S806-1 to S806-5 is not limited to this flow. For example, one, three, or more thresholds may be prepared instead of the first and second predetermined thresholds, and in addition to the predicted value of the future blood sugar level, information corresponding to respective ranges of the predicted value may be transmitted to the handheld device 110.

Next, the flowcharts shown in FIGS. 9A and 9B will be described in detail. The processing of the flowcharts shown in FIGS. 9A and 93 may be implemented in place of the processing of the flowcharts shown in FIGS. 8A and 88. When the processing of the flowchart shown in FIG. 8A is modified to the processing of the flowchart shown in FIG. 9A, the steps S801 to S807 of the flowchart shown in FIG. 8A should be replaced with steps S901 to S907 of the flowchart shown in FIG. 9A. Further, when the processing of the flowchart shown in FIG. 83 is modified to the processing of the flowchart shown in FIG. 9B, the steps S806-1 to S806-5 of the flowchart shown in FIG. 8B should be replaced with steps S906-1 to S906-9 of the flowchart shown in FIG. 9B. Furthermore, the processing of the flowcharts shown in FIGS. 9A and 9B may be implemented in parallel with the processing of the flowcharts shown in FIGS. 8A and 8B. Alternatively, the processing of the flowcharts shown in FIGS. 8A and 8B or the processing of the flowcharts shown in FIGS. 9A and 9B may be implemented selectively.

The CPU 111 of the handheld device 110 periodically transmits the user identification information stored in the user identification information storage unit 124 in the form of a signal. The access points 130 capable of receiving the signal attach the access point information allocated to each individual access point and a reception strength of the access points 130 to the user identification information, and transmit the result to the server device 140. (Step S901)

Next, the CPU 141 of the server device 140 receives the user identification information, access point information, and reception strengths transmitted via the access points in the step S901, and stores the received information in the RAM 142. The CPU 141 of the server device 140 then reads the program stored in the access point information determination unit 155 of the ROM 147 to the RAM 142, and executes the following processing. First, the CPU 141 of the server device 140 compares the reception strengths transmitted from the individual access points in the step S901. The CPU 141 of the server device 140 then selects the access point information received with the greatest reception strength and stores the selected access point information in the RAM 142 in association with the user identification information. The CPU 141 of the server device 140 then deletes the other access point information and reception strength information. Through this processing, the server device 140 obtains access point information indicating the access point to which the handheld device 110 currently belongs. (Step S902)

Next, the CPU 141 of the server device 140 refers to the database (FIG. 2B) in the access point information storage unit 152 of the auxiliary storage unit 148 to retrieve the user identification information that matches the user identification information stored in the step S902, and specifies the access point information associated with the retrieved user identification information. The CPU 141 of the server device 140 then compares the specified access point information with the access point information stored in the RAM 142. When the specified access point information and the access point information stored in the RAM 142 are different, or in other words when the CPU 141 of the server device 140 determines that the handheld device 110 has moved from the access point to which it belonged to another access point, the processing advances to a step S904. In this case, the server device 140 determines that a fluctuation has occurred in the user peripheral information. When the specified access point information and the access point information stored in the RAM 142 match, the server device 140 determines that the handheld device 110 belongs to the same access point as before. In this case, the CPU 141 of the server device 140 deletes the user identification information and access point information stored in the RAM 142 and the program read from the access point information determination unit 155, and terminates the processing. In this case, the server device 140 determines that no fluctuation has occurred in the user peripheral information. (Step S903)

Next, in steps S904 and S905, the CPU 141 of the server device 140 reads and executes the programs stored respectively in the fluctuation pattern specifying unit 157 and the biometric information prediction unit 158 in accordance with the flow of the steps S402 to S409. The CPU 141 of the server device 140 thus calculates the final predicted value of the future blood sugar level and stores the predicted value of the future blood sugar level in the RAM 142. (Steps S904, S905)

Next, the server device 140 provides the handheld device 110 with the predicted value of the future blood sugar level calculated in the step S905 and information corresponding to the access point to which the handheld device 110 currently belongs (the new access point to which the handheld device 110 is determined to have moved in the step S903). This provision processing is performed through steps S906-1 to S906-9 shown in FIG. 9B. (Step S906)

The measuring unit 112 of the handheld device 110 measures the blood sugar level of the user as the continuous user biometric information, and thus obtains blood sugar level data continuously. The transmission/reception unit 115 of the handheld device 110 transmits the blood sugar level data relating to the user, obtained continuously by the measuring unit 112, continuously to the server device 140. Next, the access point 130 receives the blood sugar level data of the user transmitted from the handheld device 110. The server device 140 then determines whether or not the access point that received the blood sugar level data of the user transmitted from the handheld device 110 is the access point 131. (Step S906-1)

When it is determined in the step S906-1 that the access point that received the blood sugar level data of the user is the access point 131, the server device 140 obtains blood sugar level reference data of the access point 131 that received the blood sugar level data of the user (step S906-4).

The server device 140 then compares the predicted value of the future blood sugar level calculated in the step S905 with the blood sugar level reference data of the access point 131 that received the blood sugar level data of the user. (Step S906-7)

The server device 140 then determines whether or not a result of the comparison between the predicted value of the future blood sugar level and the blood sugar level reference data of the access point 131 that received the blood sugar level data of the user indicates a divergence of at least a predetermined value. (Step S906-8)

When it is determined in the step S906-8 that the comparison result does not indicate a divergence of at least the predetermined value, the processing advances to the step S907. When it is determined in the step S906-8 that the comparison result indicates a divergence of at least the predetermined value, the server device 140 refers to a medical information table 300 to read unique medical information relating to the access point 131 on the basis of a sign and a degree of the divergence. The medical information table 300 is stored in the server device 140. The medical information table 300 may be stored in the ROM 147 or the auxiliary storage unit 148 of the server device 140, for example.

For example, unique medical information corresponding to the access point 131 is read from the medical information table 300 shown in FIG. 10. When the sign of the divergence is positive and the degree of divergence is small, "Eat a meal low in sugar to prevent high blood sugar" is read as the medical information. When the sign of the divergence is positive and the degree of divergence is medium, "Talk to your doctor about your insulin administration" is read as the medical information. When the sign of the divergence is positive and the degree of divergence is large, "Go to A Municipal Hospital" is read as the medical information. When the sign of the divergence is negative and the degree of divergence is small, "Eat a meal containing sugar to prevent low blood sugar" is read as the medical information. When the sign of the divergence is negative and the degree of divergence is medium, "Eat a meal containing sufficient sugar" is read as the medical information. When the sign of the divergence is negative and the degree of divergence is large, "Go to A Town Hospital" is read as the medical information.

The server device 140 transmits the medical information read from the medical information table 300 to the handheld device 110 via the transmission/reception unit 145. The medical information is received via the transmission/reception unit 115 of the handheld device 110 and displayed on the display unit 122 of the handheld device 110. For example, "Go to A Town Hospital" is displayed on the display unit 122 of the handheld device 110 as the medical information. (Step S906-9)

When it is determined in the step S906-1 that the access point that received the blood sugar level data of the user is not the access point 131, on the other hand, the processing advances to the step S906-2, where the server device 140 determines whether or not the access point that received the blood sugar level data of the user transmitted from the handheld device 110 is the access point 132. (Step S906-2)

When it is determined in the step S906-2 that the access point that received the blood sugar level data of the user is the access point 132, the server device 140 obtains the blood sugar level reference data of the access point 132 that received the blood sugar level data of the user. (Step S906-5)

The server device 140 then compares the predicted value of the future blood sugar level calculated in the step S905 with the blood sugar level reference data of the access point 132 that received the blood sugar level data of the user. (Step S906-7)

The server device 140 then determines whether or not a result of the comparison between the predicted value of the future blood sugar level and the blood sugar level reference data of the access point 132 that received the blood sugar level data of the user indicates a divergence of at least a predetermined value. (Step S906-8)

When it is determined in the step S906-8 that the comparison result does not indicate a divergence of at least the predetermined value, the processing advances to the step S907. When it is determined in the step S906-8 that the comparison result indicates a divergence of at least the predetermined value, the server device 140 refers to the medical information table 300 to read the unique medical information corresponding to the access point 132 on the basis of the sign and the degree of the divergence.

For example, the unique medical information corresponding to the access point 132 is read from the medical information table 300 shown in FIG. 10. When the sign of the divergence is positive and the degree of divergence is small, "Eat a meal low in sugar to prevent high blood sugar" is read as the medical information. When the sign of the divergence is positive and the degree of divergence is medium, "Talk to your doctor about your insulin administration and take appropriate exercise" is read as the medical information. When the sign of the divergence is positive and the degree of divergence is large, "Go to B Municipal Hospital" is read as the medical information. When the sign of the divergence is negative and the degree of divergence is small, "Eat a meal containing sugar to prevent low blood sugar" is read as the medical information. When the sign of the divergence is negative and the degree of divergence is medium, "Replenish your sugar and take appropriate exercise" is read as the medical information. When the sign of the divergence is negative and the degree of divergence is large, "Go to B Memorial Hospital" is read as the medical information.

The server device 140 transmits the medical information read from the medical information table 300 to the handheld device 110 via the transmission/reception unit 145. The medical information is received via the transmission/reception unit 115 of the handheld device 110 and displayed on the display unit 122 of the handheld device 110. For example, "Go to B Memorial Hospital" is displayed on the display unit 122 of the handheld device 110 as the medical information. (Step S906-9)

When it is determined in the step S906-2 that the access point that received the blood sugar level data of the user is not the access point 132, on the other hand, the processing advances to the step S906-3, where the server device 140 determines whether or not the access point that received the blood sugar level data of the user transmitted from the handheld device 110 is the access point 133. (Step S906-3)

When it is determined in the step S906-3 that the access point that received the blood sugar level data of the user is the access point 133, the server device 140 obtains the blood sugar level reference data of the access point 133 that received the blood sugar level data of the user. (Step S906-6)

The server device 140 then compares the predicted value of the future blood sugar level calculated in the step S905 with the blood sugar level reference data of the access point 133 that received the blood sugar level data of the user. (Step S906-7)

The server device 140 then determines whether or not a result of the comparison between the predicted value of the future blood sugar level and the blood sugar level reference data of the access point 133 that received the blood sugar level data of the user indicates a divergence of at least a predetermined value. (Step S906-8)

When it is determined in the step S906-8 that the comparison result does not indicate a divergence of at least the predetermined value, the processing advances to the step S907. When it is determined in the step S906-8 that the comparison result indicates a divergence of at least the predetermined value, the server device 140 refers to the medical information table 300 to read the unique medical information corresponding to the access point 133 on the basis of the sign and the degree of the divergence.

For example, the unique medical information corresponding to the access point 133 is read from the medical information table 300 shown in FIG. 10. When the sign of the divergence is positive and the degree of divergence is small, "Eat a meal low in sugar to prevent high blood sugar" is read as the medical information. When the sign of the divergence is positive and the degree of divergence is medium, "Talk to your doctor about your insulin administration and make sure you get enough sleep" is read as the medical information. When the sign of the divergence is positive and the degree of divergence is large, "Go to C Memorial Hospital" is read as the medical information. When the sign of the divergence is negative and the degree of divergence is small, "Eat a meal containing sugar to prevent low blood sugar" is read as the medical information. When the sign of the divergence is negative and the degree of divergence is medium, "Replenish your sugar and make sure you get enough sleep" is read as the medical information. When the sign of the divergence is negative and the degree of divergence is large, "Go to C Municipal Hospital" is read as the medical information.

The server device 140 transmits the medical information read from the medical information table 300 to the handheld device 110 via the transmission/reception unit 145. The medical information is received via the transmission/reception unit 115 of the handheld device 110 and displayed on the display unit 122 of the handheld device 110. For example, "Go to C Municipal Hospital" is displayed on the display unit 122 of the handheld device 110 as the medical information. (Step S906-9)

In the steps S906-1 to S906-9, a series of processes is performed for providing the handheld device 110 with unique medical information corresponding to respective access points 131 to 133. When this processing is complete, the processing advances to the step S907.

As described above, through the series of processes shown in FIGS. 9A and 9B, the server device 140 can receive only required information on the basis of the access point information transmitted from the handheld device 110, determine whether or not the user is in a case of lapsing into a low blood sugar condition or a high blood sugar condition in the future, and transmit the unique medical information corresponding to the access point to the handheld device 110 while suppressing wasteful charges such as communication charges as far as possible. Through this series of processes, the user is able to implement countermeasures on the basis of the transmitted information.

Further, through the series of processes shown in FIGS. 9A and 9B, the server device 140 can transmit optimum medical information unique to the area in which the user is located, which is specified from the access point, to the handheld device 110 in accordance with the blood sugar condition of the user.

Note that the server device 140 may also obtain blood sugar level data relating to other users received by the access point and averaged on the basis of gender as the blood sugar level reference data. In so doing, the blood sugar level data of the user can be compared with gender-based average reference data relating to the blood sugar condition of other users located in the area specified by the access point, and as a result, the server device 140 can transmit optimum medical information unique to the area specified by the access point to the handheld device 110.

Further, the server device 140 may also obtain blood sugar level data relating to other users received by the access point and averaged on the basis of age as the blood sugar level reference data. In so doing, the blood sugar level data of the user can be compared with age-based average reference data relating to the blood sugar condition of other users located in the area specified by the access point, and as a result, the server device 140 can transmit optimum medical information unique to the area specified by the access point to the handheld device 110.

Furthermore, the server device 140 may also obtain blood sugar level data relating to other users received by the access point and averaged on the basis of a measurement time span as the blood sugar level reference data. In so doing, the blood sugar level data of the user can be compared with measurement time span-based average reference data relating to the blood sugar condition of other users located in the area specified by the access point, and as a result, the server device 140 can transmit optimum medical information unique to the area specified by the access point to the handheld device 110.

The server device 140 may further include a blood sugar level reference data request unit so that blood sugar level reference data requested by the user can be obtained by the blood sugar level reference data request unit. For example, the user indicates desired reference data, from among the gender-based average reference data, age-based average reference data, measurement time span-based average reference data, and so on, to the blood sugar level reference data request unit. In so doing, the blood sugar level data of the user can be compared with the blood sugar level reference data desired by the user, from among the blood sugar conditions of the other users located in the area specified by the access point, and as a result, the server device 140 can transmit optimum medical information unique to the area specified by the access point to which the handheld device 110 belongs to the handheld device 110.

Furthermore, the server device 140 may transmit information indicating a lifestyle improvement to be made by the user in accordance with the result of the comparison between the blood sugar level reference data and the blood sugar level data of the user to the handheld device 110 as the medical information. In so doing, the server device 140 can transmit to the handheld device 110 information indicating a lifestyle improvement to be made by the user that is unique to the area specified by the access point to which the handheld device 110 belongs. Moreover, the server device 140 may transmit information indicating the climate, temperature, and humidity of the area in which the user is located or medical information based thereon to the handheld device 110.

In this embodiment, the processing shown in FIGS. 3, 4, and 6 to 9 may be implemented by having the CPU 141 execute individual programs stored in the ROM 147 of the server device 140 or by having the CPU 141 execute a series of programs stored in the ROM 147 of the server device 140.

This embodiment does not limit realization methods employed by the respective processing units such as the access point information determination unit 155, the biometric information profile generation unit 156, the fluctuation pattern specifying unit 157, the biometric information prediction unit 158, the user biometric information determination unit 159, the user-specific information determination unit 160, and a blood sugar level reference data acquisition unit 161. These processing units may be constituted by hardware constitutional elements, software constitutional elements, or a combination thereof using a method that can be realized by an ordinary person skilled in the art of the technical field.

The hardware constituent elements include hardware circuits, for example a field programmable gate array (FPGA), an application specific integrated circuit (ASIC), a gate array, a combination of logic gates, a signal processing circuit, an analog circuit, and so on. The software constituent elements are components (fragments) for realizing the processing described above as software, but are not limited to a language, a development environment, and so on for realizing the software. The software constituent elements include tasks, processes, threads, drivers, firmware, databases, tables, functions, procedures, sub-routines, predetermined parts of program code, data structures, arrays, variables, parameters, and so on. These software constituent elements are realized in a computer on one or a plurality of memories or realized by executing data on one or a plurality of memories using one or a plurality of processors (for example, a CPU (Central Processing Unit), a DSP (Digital Signal Processor), or the like).

(Description Relating to Computer-Readable Medium)

Any of the functions of the embodiment described above may be encoded and stored in a storage area of a computer-readable medium. In this case, a program for realizing the function may be provided to the computer, or to a computer incorporated into a machine or an apparatus, via the computer-readable medium. The function can be realized by having the computer, or the computer incorporated into a machine or an apparatus, read the program from the storage area of the computer-readable medium and execute the program.

Here, the computer-readable medium denotes a recording medium that employs an electric, magnetic, optical, chemical, physical, or mechanical action to accumulate information such as programs and data and holds the information in a condition that allows reading thereof to a computer. A flexible disk, a magneto-optical disk, a CD-ROM, a CD-R/W, a DVD, a DAT, 8 mm tape, a memory card, and so on may be cited as examples of recording media that can be attached to and detached from a computer. Further, a hard disk, a ROM, and so on may be cited as recording media that are fixed to a computer.

INDUSTRIAL APPLICABILITY

According to the present invention, a server device can receive required continuous user biometric information at a required time not only during an emergency, but also in accordance with a fluctuation in user peripheral information that affects the continuous user biometric information, for example variation in events occurring during everyday life such as eating, sleep, bathing, exercise, and medicine administration, or variation in dietary habits and environmental variation such as climate variation accompanying a move to another area, and the server device can select information desired by a user on the basis of this information and provide the user with the information reliably.

DESCRIPTION OF THE REFERENCE NUMERALS AND SYMBOLS 110 handheld device
111 CPU (of handheld device)
112 measuring unit
113 analog signal processing unit
114 A/D conversion unit
115 transmission/reception unit (of handheld device)
116 auxiliary storage unit (of handheld device)
117 ROM (of handheld device)
118 RAM (of handheld device)
119 EEPROM (of handheld device)
120 clock (of handheld device)
121 gate array (of handheld device)
122 display unit (of handheld device)
123 input unit (of handheld device)
124 user identification information storage unit
125 user-specific information storage unit (of handheld device)
126 measurement data storage unit
127 calibration curve data storage unit
128 modem (of handheld device)
129 NCU (of handheld device)
130 access point
131 to 133 access points disposed in respective areas
134 communication network
140 server device
141 CPU (of server device)
142 RAM (of server device)
143 NCU (of server device)
144 modem (of server device)
145 transmission/reception unit (of server device)
146 EEPROM (of server device)
147 ROM (of server device)
148 auxiliary storage unit (of server device)
149 clock (of server device)
150 user-specific information storage unit (of server device)
151 user biometric information storage unit
152 access point information storage unit
153 profile generation storage unit
154 access point area information storage unit
155 access point information determination unit
156 biometric information profile generation unit
157 fluctuation pattern specifying unit
158 biometric information prediction unit
159 user biometric information determination unit
160 user-specific information determination unit
161 blood sugar level reference data acquisition unit

The invention claimed is:

1. An information provision system comprising
a handheld device and
a server device comprising a biometric information storage unit,
wherein the handheld device transmits user peripheral information to the server device and receives information transmitted from the server device, and
wherein
the server device processes continuously generated user biometric information by measuring the user biometric information continuously from the handheld device, storing the measured biometric information in the biometric information storage unit and calculating a predicted value of future user biometric information from the stored and continuously received user biometric information after determining that a fluctuation has occurred in the user peripheral information, or performs processing for receiving a predicted value of the future user biometric information from the handheld device after determining that a fluctuation has occurred in the user peripheral information, and
on the basis of the predicted value of each of the future user biometric information and the user peripheral information, the server device selects information and transmits the selected information to the handheld device,
wherein
a fluctuation pattern specifying unit stores a program that enables processing for specifying a fluctuation pattern in the past user biometric information that matches a fluctuation pattern in recent user biometric information of the user from the user-specific biometric information profile stored in a profile generation storage unit;
a biometric information prediction unit stores a program for calculating a predicted value of future user biometric information by adding a fluctuation value of the future user biometric information, which is associated with the fluctuation pattern in the past user biometric information specified by the fluctuation pattern specifying unit, to current user biometric information,
wherein
the user biometric information determination unit stores a program for determining whether or not a divergence of at least a predetermined width exists between the user biometric information of the handheld device and the user biometric information stored in the user biometric information storage unit of the server device and, when the divergence of at least the predetermined width exists, executing programs stored respectively in the fluctuation pattern specifying unit and the biometric information prediction unit to calculate the predicted value of the future user biometric information, and transmitting required information to the handheld device on the basis of the predicted value.

2. The information provision system according to claim 1, wherein
the user peripheral information partially includes the continuously received user biometric information, and
a fluctuation is determined to have occurred in the user peripheral information when at least a predetermined divergence width exists between the user biometric information stored in the user biometric information storage unit of the server device and the user peripheral information transmitted from the handheld device.

3. The information provision system according to claim 2, wherein selecting the information includes determining whether the predicted value of the future user biometric information is equal to or smaller than a first predetermined threshold or equal to or larger than a second predetermined threshold.

4. The information provision system according to claim 1, wherein
the user peripheral information is user-specific information stored in a user-specific information storage unit of the handheld device,
the biometric information storage unit of the server device stores the user-specific information, and
a fluctuation is determined to have occurred in the user peripheral information when the user-specific information stored in the user-specific biometric information storage unit of the server device differs from the user peripheral information transmitted from the handheld device.

5. The information provision system according to claim 1, wherein
the user peripheral information comprises access point information indicating an access point to which the handheld device currently belongs,
the biometric information storage unit of the server device stores the access point information, and
a fluctuation is determined to have occurred in the user peripheral information when the access point information stored in the access point information storage unit of the server device differs from the user peripheral information.

6. The information provision system according to claim 1, wherein when the predicted value of the future user biometric information is calculated from the continuously received user biometric information,
the handheld device or the server device comprises the biometric information profile generation unit, the fluctuation pattern specifying unit, and the biometric information prediction unit.

7. An information provision method comprising
a handheld device and
a server device,
wherein the handheld device transmits user peripheral information to the server device and receives information transmitted from the server device, and
wherein the server device executes:
a step of determining whether a fluctuation has occurred in the user peripheral information;
a step of receiving continuously generated user biometric information by continuously measuring the user biometric information from the handheld device and calculating a predicted value of future user biometric information from the user biometric information after determining that a fluctuation has occurred in the user peripheral information, or receiving the predicted value of the future user biometric information from the handheld device after determining that a fluctuation has occurred in the user peripheral information;
a step of selecting information on the basis of the predicted value of the future user biometric information and the user peripheral information; and
a step of transmitting the selected information to the handheld device,
wherein
a fluctuation pattern specifying unit stores a program that enables processing for specifying a fluctuation pattern in the past user biometric information that matches a fluctuation pattern in recent user biometric information of the user from the user-specific biometric information profile stored in a profile generation storage unit;
a biometric information prediction unit stores a program for calculating a predicted value of future user biometric information by adding a fluctuation value of the future user biometric information, which is associated with the fluctuation pattern in the past user biometric information specified by the fluctuation pattern specifying unit, to current user biometric information,
wherein
the user biometric information determination unit stores a program for determining whether or not a divergence of at least a predetermined width exists between the user biometric information of the handheld device and the user biometric information stored in the user biometric information storage unit of the server device and, when the divergence of at least the predetermined width exists, executing programs stored respectively in the fluctuation pattern specifying unit and the biometric information prediction unit to calculate the predicted value of the future user biometric information, and transmitting required information to the handheld device on the basis of the predicted value.

8. A server device, wherein the server device receives user peripheral information transmitted from a handheld device and transmits the information to the handheld device,
the server device comprising a determination unit for determining whether a fluctuation has occurred in the user peripheral information, and wherein
the determination unit processes continuously received user biometric information by measuring the user biometric information continuously from the handheld device and calculating a predicted value of future user biometric information from the received user biometric information after determining that a fluctuation has occurred in the user peripheral information, or processes the received predicted value of the future user biometric information from the handheld device after determining that a fluctuation has occurred in the user peripheral information, and
on the basis of the predicted value of the future user biometric information and the user peripheral information, the determination unit selects information and transmits the selected information to the handheld device,
wherein
a fluctuation pattern specifying unit stores a program that enables processing for specifying a fluctuation pattern in the past user biometric information that matches a fluctuation pattern in recent user biometric information of the user from the user-specific biometric information profile stored in a profile generation storage unit;
a biometric information prediction unit stores a program for calculating a predicted value of future user biometric information by adding a fluctuation value of the future user biometric information, which is associated with the fluctuation pattern in the past user biometric information specified by the fluctuation pattern specifying unit, to current user biometric information,
wherein
the user biometric information determination unit stores a program for determining whether or not a divergence of at least a predetermined width exists between the user biometric information of the handheld device and the user biometric information stored in the user biometric information storage unit of the server device and, when the divergence of at least the predetermined width exists, executing programs stored respectively in the fluctuation pattern specifying unit and the biometric information prediction unit to calculate the predicted value of the future user biometric information, and transmitting required information to the handheld device on the basis of the predicted value.

9. The server device according to claim 8, wherein
the user peripheral information partially includes the continuously received user biometric information.

10. The server device according to claim 9, wherein the information selection performed in the determination unit further includes determining whether the predicted value of the future user biometric information is equal to or smaller than a first predetermined threshold or equal to or larger than a second predetermined threshold.

11. The server device according to claim 8, wherein
the user peripheral information comprises user-specific information stored in a user-specific information storage unit of the handheld device,
the biometric information storage unit of the server device stores the user-specific information, and
the determination unit determines that a fluctuation has occurred in the user peripheral information when the user-specific information stored in the user-specific information storage unit differs from the user peripheral information transmitted from the handheld device.

12. The server device according to claim 8, wherein
the user peripheral information comprises access point information indicating an access point to which the handheld device currently belongs,
the biometric information storage unit of the server device stores the access point information, and
the determination unit determines that a fluctuation has occurred in the user peripheral information when the access point information stored in the access point information storage unit differs from the user peripheral information.

* * * * *